(12) United States Patent
Voerman

(10) Patent No.: US 6,270,808 B1
(45) Date of Patent: *Aug. 7, 2001

(54) ANTI-VIRAL ISOLATES OBTAINABLE FROM LEECHES

(76) Inventor: Gerard Voerman, Binnenhof 21, B-2930 Brasschaat (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,417

(22) PCT Filed: Nov. 13, 1996

(86) PCT No.: PCT/NL96/00444

§ 371 Date: Jul. 7, 1998

§ 102(e) Date: Jul. 7, 1998

(87) PCT Pub. No.: WO97/17981

PCT Pub. Date: May 22, 1997

(30) Foreign Application Priority Data

Nov. 13, 1995 (NL) .................................. 95203099

(51) Int. Cl.$^7$ .................................................. A61K 35/60
(52) U.S. Cl. ........................ 424/520; 435/235.1; 514/730
(58) Field of Search ........................ 424/520; 435/235.1; 514/730

(56) References Cited

U.S. PATENT DOCUMENTS

| 5,196,438 | 3/1993 | Martin et al. . |
| 5,246,715 | 9/1993 | Orevi et al. . |
| 5,972,698 | * 10/1999 | Fritz et al. . |

FOREIGN PATENT DOCUMENTS

| 44 12 174 A1 | 10/1995 | (DE) . |
| 0 541 168 B1 | 5/1993 | (EP) . |
| 0 558 630 B1 | 9/1993 | (EP) . |
| 0 666 842 B1 | 8/1995 | (EP) . |
| WO 94/06454 | 3/1994 | (WO) . |
| WO 95/14011 | 5/1995 | (WO) . |
| WO 95/16688 | 6/1995 | (WO) . |
| WO 95/20384 | 8/1995 | (WO) . |
| WO 96/13585 | 5/1996 | (WO) . |

OTHER PUBLICATIONS

Sommerhoff et al. Biol. Chem Hoppe–Seyler. vol. 375(10). pp 685–694, 1994.*

J.E.F. Reynolds: "M, The Extra Pharmacopeia", The Pharmaceutical Press, London 1993. pp. 555–563.

* cited by examiner

Primary Examiner—Leon B. Lankford, Jr.
(74) Attorney, Agent, or Firm—Merchant & Gould P.C.

(57) ABSTRACT

Methods substances and composition derived from leeches, bacteria associated with leeches, or combinations thereof are provided to prevent retroviral infections of host cells. More particularly, the invention relates to the inhibition of HIV replication. Thus the invention provides methods and substances for treating and/or preventing HIV infection and/or AIDS. The compounds or mixtures are obtainable by solvent extraction techniques and separation steps and were tested in the following manner. Two syncytium-forming HIV isolates HIV AMS55 and HIV Ams37 were inoculated in PBMC and monocytes. During 14 days HIV induced cytopathic effects (CPE) (syncytium formation) and the virus production as determined by a p24 capture ELISA was monitored, after addition of leech head extracts. The results of these tests with the partly purified HIV inhibiting substance or substances is as follows: 3 fractions inhibited both syncytium formation and p24 antigen by 100% at a concentration of: 0.67 $\mu$M, 0.5 $\mu$M and 0.17 $\mu$M respectively in both HIV isolates. A fourth fraction underwent dilution series and inhibited both CPE and p—24 antigen 100% from 0.5 $\mu$M upwards in both HIV isolates.

24 Claims, 52 Drawing Sheets

FIG. 1

Figure 8:
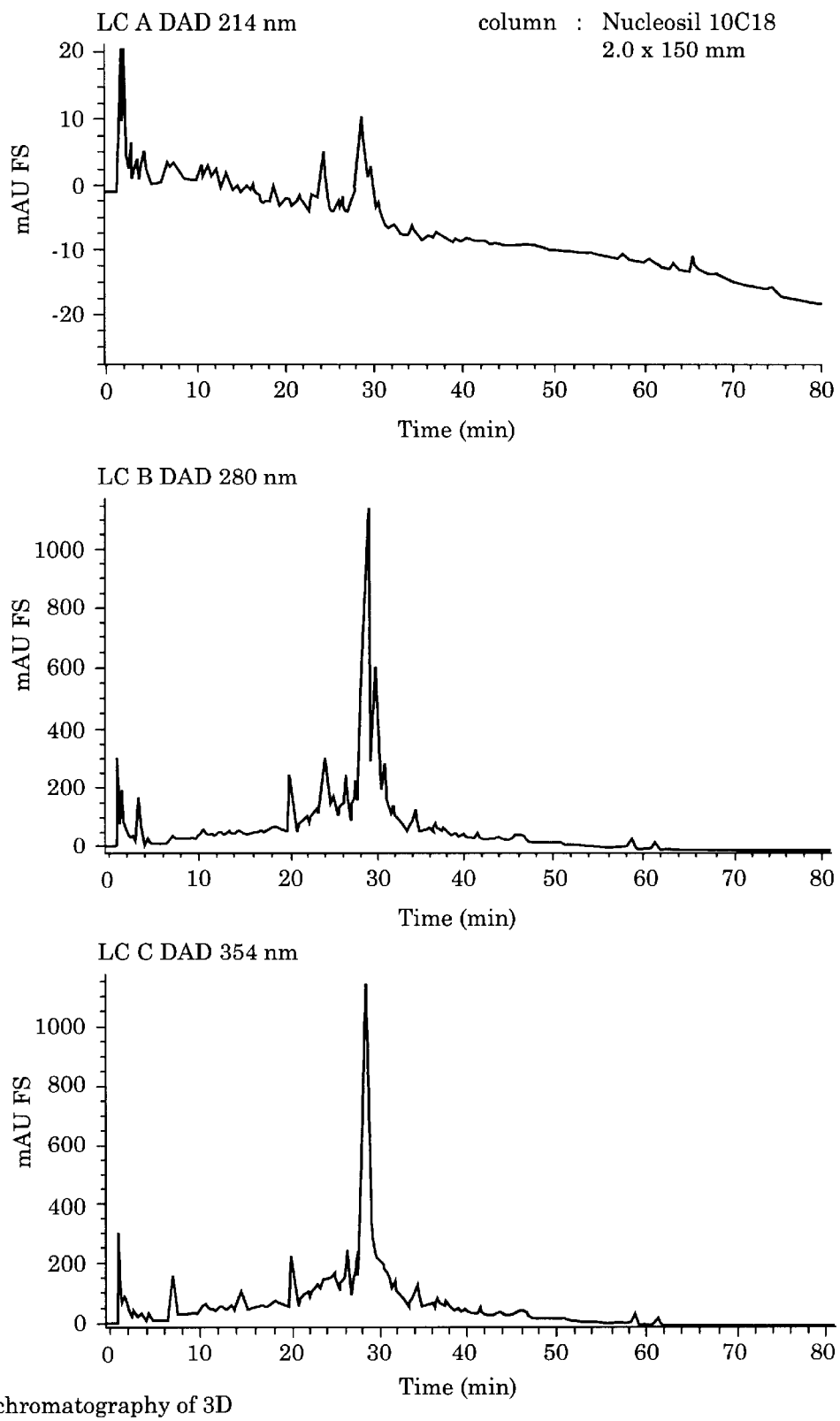

Assay: Effect of a protease inhibitor on HIV-1 infection in vitro

Table 1
Substance 3 leech head extract

| Primary HIV-1 isolate $HIV_{Ams}$ 37 | | | | | | |
|---|---|---|---|---|---|---|
| Inoculum ($TCID_{50}$/ml): | $10^4$ | | | | | |
| Concentration of substance ($\mu$M) | CPE | | Day 7 | | Day 14 | |
| | Day 4 | Day 7 | p24 ($\mu$g/ml) | Percentage Inhibition | p24 ($\mu$g/ml) | Percentage Inhibition |
| 0 | +++ | +++ | 0.85 | | 0.58 | |
| 0.063 | ++ | +++ | 0.71 | 16 | 0.55 | 5 |
| 0.125 | +++ | +++ | 0.51 | 40 | 0.40 | 31 |
| 0.25 | − | +++ | 0.31 | 64 | 0.27 | 53 |
| 0.5 | − | ± | ≤ 0.05 | ≥ 94 | 0.15 | 74 |

Table 2
Substance 3 leech head extract

| Primary HIV-1 isolate $HIV_{Ams}$ 55 | | | | | | |
|---|---|---|---|---|---|---|
| Inoculum ($TCID_{50}$/ml): | $10^4$ | | | | | |
| Concentration of substance ($\mu$M) | CPE | | Day 7 | | Day 14 | |
| | Day 4 | Day 7 | p24 ($\mu$g/ml) | Percentage Inhibition | p24 ($\mu$g/ml) | Percentage Inhibition |
| 0 | +++ | +++ | 1.46 | | 0.62 | |
| 0.063 | +++ | +++ | 1.42 | 3 | 0.70 | -13 |
| 0.125 | +++ | +++ | 1.25 | 14 | 0.59 | 5 |
| 0.25 | + | +++ | 1.07 | 27 | 0.65 | -5 |
| 0.5 | | +++ | 0.05 | 97 | 0.64 | 3 |

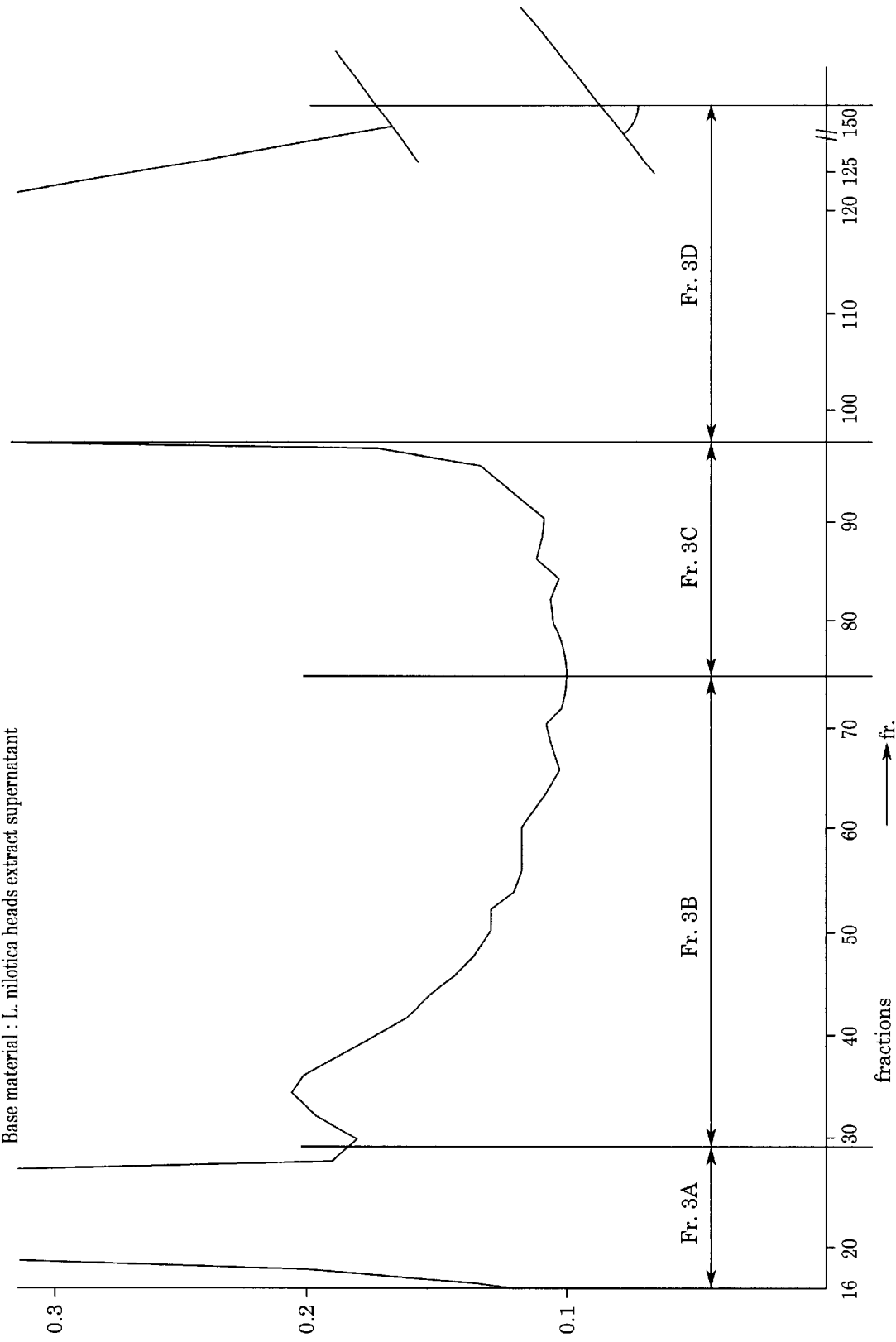

FIG. 3

SDS-PAGE of fractions from L nilotica head extract supernatant

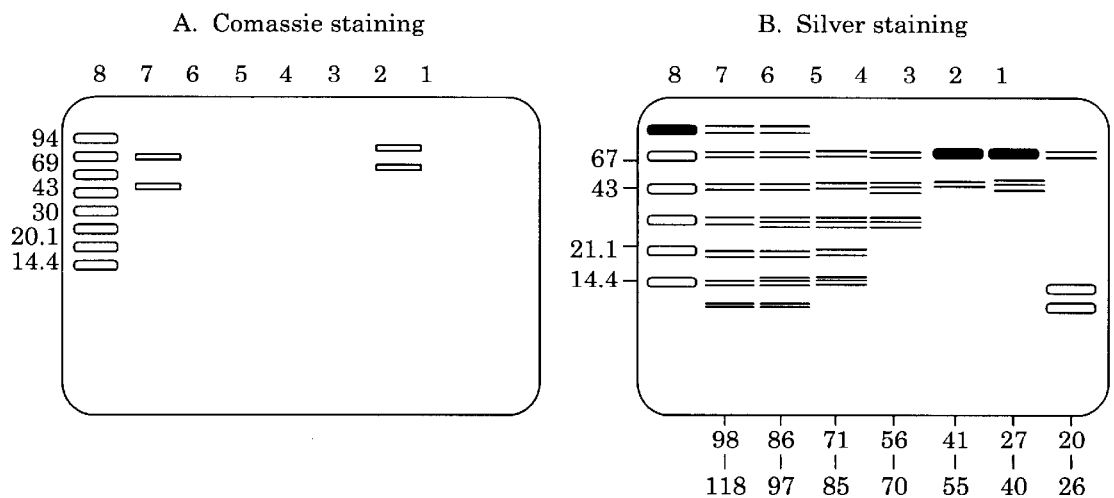

```
Remarks:    Lane 1:  fraction  20 to 26
            Lane 2:  "    "    27 to 40
            Lane 3:  "    "    40 to 55
            Lane 4:  "    "    56 to 70
            Lane 5:  "    "    71 to 85
            Lane 6:  "    "    86 to 97
            Lane 7:  "    "    98 to 118
            Lane 8:  reference proteins.
```

Volumina taken from Sephadex chromatography were:

```
fraction 20 to 26  :  20 ηl
"   "   " 27 to 40 :   8 ηl
"   "   " 40 to 97 :   7 ηl
"   "   " 98 to 118:   4 ηl
```

Lane 2 and 3 yield predominantly bands at ca. 67 kDa.
Lane 4 and 5 yield predominantly bands at ca. 43 kDa.
Lane 6 and 7 yield predominantly bands at 10 to 15 kDA.
Lane 1 yields predominantly a band of ca. 5 kDa.

FIG. 4

Assay: Effect of a protease inhibitor on HIV-1 infection in vitro

Table 3
Fraction A

| Primary HIV-1 isolate HIV$_{Ams}$ 37 | | | | | |
|---|---|---|---|---|---|
| Inoculum (TCID$_{50}$/ml): | $10^4$ | | | | |
| Concentration of substance ($\mu$M) | CPE | | Day 7 | | Day 14 | |
| | Day 4 | Day 7 | p24 ($\mu$g/ml) | Percentage Inhibition | p24 ($\mu$g/ml) | Percentage Inhibition |
| 0 | + | + + + + | 0.34 | | 0.19 | |
| 0.063 | + + | + + + + | 0.26 | 24 | 0.18 | 5 |
| 0.125 | + + | + + + + | 0.28 | 18 | 0.17 | 11 |
| 0.25 | + + + + | + + + + | 0.30 | 12 | 0.15 | 21 |
| 0.5 | - | + + + + | 0.28 | 18 | 0.17 | 11 |

Table 4
Fraction A

| Primary HIV-1 isolate HIV$_{Ams}$ 55 | | | | | |
|---|---|---|---|---|---|
| Inoculum (TCID$_{50}$/ml): | $10^4$ | | | | |
| Concentration of substance ($\mu$M) | CPE | | Day 7 | | Day 14 | |
| | Day 4 | Day 7 | p24 ($\mu$g/ml) | Percentage Inhibition | p24 ($\mu$g/ml) | Percentage Inhibition |
| 0 | + + | + + + + | 0.23 | | 0.18 | |
| 0.063 | + + + + | + + + + | 0.23 | 0 | 0.18 | 0 |
| 0.125 | + + + | + + + + | 0.29 | -26 | 0.16 | 11 |
| 0.25 | + + + + | + + + + | 0.33 | -43 | 0.17 | 6 |
| 0.5 | + + + + | + + + + | 0.34 | -48 | 0.20 | -11 |

FIG. 5

Assay: Effect of a protease inhibitor on HIV-1 infection in vitro

Table 5
Fraction B

| Primary HIV-1 isolate $HIV_{Ams}$ 37 | | | | | |
|---|---|---|---|---|---|
| Inoculum ($TCID_{50}$/ml): | $10^4$ | | | | |
| Concentration of substance ($\mu M$) | CPE | | Day 7 | | Day 14 | |
| | Day 4 | Day 7 | p24 ($\mu$g/ml) | Percentage Inhibition | p24 ($\mu$g/ml) | Percentage Inhibition |
| 0 | + | + + + + | 0.23 | | 0.18 | |
| 0.063 | + + | + + + + | 0.25 | -9 | 0.20 | -11 |
| 0.125 | + + | + + + + | 0.25 | -9 | 0.18 | 0 |
| 0.25 | + + + | + + + + | 0.24 | -4 | 0.17 | 6 |
| 0.5 | + + + | + + + + | 0.28 | -22 | 0.18 | 0 |

Table 6
Fraction B

| Primary HIV-1 isolate $HIV_{Ams}$ 55 | | | | | |
|---|---|---|---|---|---|
| Inoculum ($TCID_{50}$/ml): | $10^4$ | | | | |
| Concentration of substance ($\mu M$) | CPE | | Day 7 | | Day 14 | |
| | Day 4 | Day 7 | p24 ($\mu$g/ml) | Percentage Inhibition | p24 ($\mu$g/ml) | Percentage Inhibition |
| 0 | + + + + | + + + + | 0.21 | | 0.18 | |
| 0.063 | + + + + | + + + + | 0.30 | -43 | 0.16 | 11 |
| 0.125 | + + + + | + + + + | 0.28 | -33 | 0.17 | 6 |
| 0.25 | + + + + | + + + + | 0.27 | -29 | 0.16 | 11 |
| 0.5 | + + + + | + + + + | 0.32 | -52 | 0.17 | 6 |

FIG. 6

Assay: Effect of a protease inhibitor on HIV-1 infection in vitro

Table 7
Fraction C

| Primary HIV-1 isolate HIV$_{Ams}$ 37 | | | | | | |
|---|---|---|---|---|---|---|
| Inoculum (TCID$_{50}$/ml): | $10^4$ | | | | | |
| Concentration of substance ($\mu$M) | CPE | | Day 7 | | Day 14 | |
| | Day 4 | Day 7 | p24 ($\mu$g/ml) | Percentage Inhibition | p24 ($\mu$g/ml) | Percentage Inhibition |
| 0 | ++ | ++++ | 0.24 | | 0.16 | |
| 0.063 | ++ | ++++ | 0.28 | -17 | 0.19 | -19 |
| 0.125 | +++ | ++++ | 0.25 | -4 | 0.16 | 0 |
| 0.25 | ++++ | ++++ | 0.26 | -8 | 0.17 | -6 |
| 0.5 | ++++ | ++++ | 0.28 | -17 | 0.18 | -13 |

Table 8
Fraction C

| Primary HIV-1 isolate HIV$_{Ams}$ 55 | | | | | | |
|---|---|---|---|---|---|---|
| Inoculum (TCID$_{50}$/ml): | $10^4$ | | | | | |
| Concentration of substance ($\mu$M) | CPE | | Day 7 | | Day 14 | |
| | Day 4 | Day 7 | p24 ($\mu$g/ml) | Percentage Inhibition | p24 ($\mu$g/ml) | Percentage Inhibition |
| 0 | +++ | ++++ | 0.19 | | 0.17 | |
| 0.063 | ++++ | ++++ | 0.26 | -37 | 0.18 | -6 |
| 0.125 | ++++ | ++++ | 0.30 | -58 | 0.17 | 0 |
| 0.25 | ++++ | ++++ | 0.31 | -63 | 0.16 | -6 |
| 0.5 | ++++ | ++++ | 0.32 | -68 | 0.21 | -24 |

FIG. 7

Assay: Effect of a protease inhibitor on HIV-1 infection in vitro

Table 9
Fraction D

| Primary HIV-1 isolate $HIV_{Ams}$ 37 | | | | | | |
|---|---|---|---|---|---|---|
| Inoculum ($TCID_{50}$/ml): | $10^4$ | | | | | |
| Concentration of substance ($\mu$M) | CPE | | Day 7 | | Day 14 | |
| | Day 4 | Day 7 | p24 ($\mu$g/ml) | Percentage Inhibition | p24 ($\mu$g/ml) | Percentage Inhibition |
| 0 | ++++ | ++++ | 0.21 | | 0.21 | |
| 0.063 | ++ | ++++ | 0 | 100 | 0.05 | 76 |
| 0.125 | – | – | 0 | 100 | 0 | 100 |
| 0.25 | – | – | 0 | 100 | 0 | 100 |
| 0.5 | – | – | 0 | 100 | 0 | 100 |

Table 10
Fraction D

| Primary HIV-1 isolate $HIV_{Ams}$ 55 | | | | | | |
|---|---|---|---|---|---|---|
| Inoculum ($TCID_{50}$/ml): | $10^4$ | | | | | |
| Concentration of substance ($\mu$M) | CPE | | Day 7 | | Day 14 | |
| | Day 4 | Day 7 | p24 ($\mu$g/ml) | Percentage Inhibition | p24 ($\mu$g/ml) | Percentage Inhibition |
| 0 | +++ | ++++ | 0.21 | | 0.16 | |
| 0.063 | ++ | ++++ | 0 | 100 | 0.21 | -31 |
| 0.125 | – | + | 0 | 100 | 0.02 | 88 |
| 0.25 | – | – | 0 | 100 | 0 | 100 |
| 0.5 | – | – | 0 | 100 | 0 | 100 |

HPLC chromatography of 3D

HPLC Chromatography with division in fractions 3D1, 3D2, 3D3 and 3D4.

Assay: Effect of a protease inhibitor on HIV-1 infection in vitro

Table 11
Subfraction D1

| Primary HIV-1 isolate HIV$_{Ams}$37 | | | | | | | | | | | | | |
|---|---|---|---|---|---|---|---|---|---|---|---|---|---|
| Inoculum (TCID$_{50}$/ml): | $10^3$ | | | | | | $10^4$ | | | | | | |
| Concentration of substance (µM) | CPE | | Day 7 | | Day 14 | | CPE | | Day 7 | | Day 14 | | |
| | Day 5 | Day 7 | p24 (µg/ml) | Percentage Inhibition | p24 (µg/ml) | Percentage Inhibition | Day 4 | Day 7 | p24 (µg/ml) | Percentage Inhibition | p24 (µg/ml) | Percentage Inhibition | |
| 0 | – | ++++ | – | | 0.19 | | + | ++++ | 0.20 | | 0.21 | | |
| 0.063 | nt | +++ | – | N.A. | 0.23 | -21 | nt | ++++ | 0.12 | 40 | 0.24 | -14 | |
| 0.125 | nt | +++ | – | N.A. | 0.19 | 0 | nt | ++++ | 0.16 | 20 | 0.23 | -10 | |
| 0.25 | nt | ++ | – | N.A. | 0.22 | -16 | nt | ++++ | 0.22 | -10 | 0.25 | -19 | |
| 0.5 | nt | ++++ | – | N.A. | 0.21 | -11 | nt | ++++ | 0.17 | 15 | 0.24 | -14 | |

FIG. 11

FIG. 12

Assay: Effect of a protease inhibitor on HIV-1 infection in vitro

Table 12
Subfraction D1

Primary HIV-1 isolate HIV$_{Ams}$ 55

| Inoculum (TCID$_{50}$/ml): | $10^3$ | | | | | | | $10^4$ | | | | | | |
|---|---|---|---|---|---|---|---|---|---|---|---|---|---|---|
| | CPE | | Day 7 | | Day 14 | | | CPE | | Day 7 | | Day 14 | | |
| Concentration of substance (μM) | Day 5 | Day 7 | p24 (μg/ml) | Percentage Inhibition | p24 (μg/ml) | Percentage Inhibition | | Day 4 | Day 7 | p24 (μg/ml) | Percentage Inhibition | p24 (μg/ml) | Percentage Inhibition | |
| 0 | – | ++++ | – | | 0.25 | | | ++ | ++++ | 0.21 | | 0.33 | | |
| 0.063 | nt | ++++ | – | N.A. | 0.30 | -20 | | nt | +++ | 0.19 | 10 | 0.37 | -12 | |
| 0.125 | nt | ++++ | – | N.A. | 0.30 | -20 | | nt | ++++ | 0.21 | 0 | 0.38 | -15 | |
| 0.25 | nt | +++ | – | N.A. | 0.30 | -20 | | nt | ++++ | 0.18 | 14 | 0.31 | 6 | |
| 0.5 | nt | ++++ | – | N.A. | 0.24 | 4 | | nt | ++++ | 0.17 | 19 | 0.32 | 3 | |

FIG. 13

Assay: Effect of a protease inhibitor on HIV-1 infection in vitro

Table 13
Subfraction D2

Primary HIV-1 isolate HIV$_{Ams}$$^{37}$

| Inoculum (TCID$_{50}$/ml): | $10^3$ | | | | | | | | $10^4$ | | | | | | | |
|---|---|---|---|---|---|---|---|---|---|---|---|---|---|---|---|---|
| Concentration of substance (µM) | CPE | | | Day 7 | | Day 14 | | | CPE | | | Day 7 | | Day 14 | |
| | Day 5 | Day 7 | | p24 (µg/ml) | Percentage Inhibition | p24 (µg/ml) | Percentage Inhibition | | Day 4 | Day 7 | | p24 (µg/ml) | Percentage Inhibition | p24 (µg/ml) | Percentage Inhibition |
| 0 | – | ++++ | | – | | 0.19 | | | + | ++++ | | 0.20 | | 0.21 | |
| 0.063 | nt | ++++ | | – | N.A. | 0.26 | -37 | | nt | ++++ | | 0.20 | 0 | 0.24 | -14 |
| 0.125 | nt | +++ | | – | N.A. | 0.23 | -21 | | nt | ++++ | | 0.23 | -15 | 0.22 | -5 |
| 0.25 | nt | ++++ | | – | N.A. | 0.20 | -5 | | nt | ++++ | | 0.22 | -10 | 0.23 | -10 |
| 0.5 | nt | ++++ | | – | N.A. | 0.24 | -26 | | nt | ++++ | | 0.23 | -15 | 0.20 | 5 |

FIG. 14

Assay: Effect of a protease inhibitor on HIV-1 infection in vitro

Table 14
Subfraction D2

| Primary HIV-1 isolate HIV$_{Ams}$55 | | | | | | | | | | | |
|---|---|---|---|---|---|---|---|---|---|---|---|
| Inoculum (TCID$_{50}$/ml): | $10^3$ | | | | | | $10^4$ | | | | |
| | CPE | | Day 7 | | Day 14 | | CPE | | Day 7 | | Day 14 | |
| Concentration of substance ($\mu$M) | Day 5 | Day 7 | p24 ($\mu$g/ml) | Percentage Inhibition | p24 ($\mu$g/ml) | Percentage Inhibition | Day 4 | Day 7 | p24 ($\mu$g/ml) | Percentage Inhibition | p24 ($\mu$g/ml) | Percentage Inhibition |
| 0 | – | ++++ | – | | 0.25 | | ++ | ++++ | 0.21 | | 0.33 | |
| 0.063 | nt | ++++ | – | N.A. | 0.27 | -8 | nt | ++++ | 0.15 | 29 | 0.33 | 0 |
| 0.125 | nt | ++++ | – | N.A. | 0.29 | -16 | nt | ++++ | 0.21 | 0 | 0.31 | 6 |
| 0.25 | nt | ++++ | – | N.A. | 0.31 | -24 | nt | ++++ | 0.19 | 10 | 0.24 | 27 |
| 0.5 | nt | ++++ | – | N.A. | 0.21 | 16 | nt | ++++ | 0.18 | 14 | 0.22 | 33 |

FIG. 15

Assay: Effect of a protease inhibitor on HIV-1 infection in vitro

Table 15
Subfraction D3

| Primary HIV-1 isolate HIV$_{Ams}$$^{37}$ | | | | | | | | | | | | |
|---|---|---|---|---|---|---|---|---|---|---|---|---|
| Inoculum (TCID$_{50}$/ml): | $10^3$ | | | | | | $10^4$ | | | | | |
| | CPE | | Day 7 | | Day 14 | | CPE | | Day 7 | | Day 14 | |
| Concentration of substance (µM) | Day 5 | Day 7 | p24 (µg/ml) | Percentage Inhibition | p24 (µg/ml) | Percentage Inhibition | Day 4 | Day 7 | p24 (µg/ml) | Percentage Inhibition | p24 (µg/ml) | Percentage Inhibition |
| 0 | – | ++++ | – | | 0.19 | | + | ++++ | 0.20 | | 0.21 | |
| 0.063 | nt | ++++ | – | N.A. | 0.28 | -47 | nt | ++++ | 0.16 | 20 | 0.26 | -24 |
| 0.125 | nt | + | – | N.A. | 0.13 | 32 | nt | + | 0.07 | 65 | 0.17 | 19 |
| 0.25 | nt | – | – | N.A. | – | 100 | nt | – | – | 100 | – | 100 |
| 0.5 | nt | – | – | N.A. | – | 100 | nt | – | – | 100 | – | 100 |

FIG. 16

Assay: Effect of a protease inhibitor on HIV-1 infection in vitro

Table 16
Subfraction D3
Primary HIV-1 isolate HIV$_{Ams}$ 55

| Inoculum (TCID$_{50}$/ml): | 10$^3$ | | | | | | 10$^4$ | | | | | |
|---|---|---|---|---|---|---|---|---|---|---|---|---|
| | CPE | | Day 7 | | Day 14 | | CPE | | Day 7 | | Day 14 | |
| Concentration of substance (μM) | Day 5 | Day 7 | p24 (μg/ml) | Percentage Inhibition | p24 (μg/ml) | Percentage Inhibition | Day 4 | Day 7 | p24 (μg/ml) | Percentage Inhibition | p24 (μg/ml) | Percentage Inhibition |
| 0 | − | ++++ | − | N.A. | 0.25 | | ++ | ++++ | 0.21 | | 0.33 | |
| 0.063 | nt | ++++ | − | N.A. | 0.37 | -48 | nt | ++++ | 0.25 | -19 | 0.38 | -15 |
| 0.125 | nt | +++ | − | N.A. | 0.12 | 52 | nt | ++++ | 0.20 | 5 | 0.29 | 12 |
| 0.25 | nt | − | − | N.A. | − | 100 | nt | +++ | − | 100 | − | 100 |
| 0.5 | nt | − | − | N.A. | − | 100 | nt | − | − | 100 | − | 100 |

FIG. 17

Assay: Effect of a protease inhibitor on HIV-1 infection in vitro

Table 17
Fraction D4

Primary HIV-1 isolate HIV$_{Ams}$$^{37}$

| Inoculum (TCID$_{50}$/ml): | $10^3$ | | | | | | $10^4$ | | | | | |
|---|---|---|---|---|---|---|---|---|---|---|---|---|
| | CPE | | Day 7 | | Day 14 | | CPE | | Day 7 | | Day 14 | |
| Concentration of substance (μM) | Day 5 | Day 7 | p24 (μg/ml) | Percentage Inhibition | p24 (μg/ml) | Percentage Inhibition | Day 4 | Day 7 | p24 (μg/ml) | Percentage Inhibition | p24 (μg/ml) | Percentage Inhibition |
| 0 | – | ++++ | – | | 0.19 | | + | ++++ | 0.20 | | 0.21 | |
| 0.063 | nt | – | – | N.A. | – | 100 | nt | – | – | 100 | – | 100 |
| 0.125 | nt | – | – | N.A. | – | 100 | nt | – | – | 100 | – | 100 |
| 0.25 | nt | – | – | N.A. | – | 100 | nt | – | – | 100 | – | 100 |
| 0.5 | nt | – | – | N.A. | – | 100 | nt | – | – | 100 | – | 100 |

FIG. 18

Assay: Effect of a protease inhibitor on HIV-1 infection in vitro

Table 18
Fraction D4
Primary HIV-1 isolate HIV$_{Ams}$55

| Inoculum (TCID$_{50}$/ml): | $10^3$ | | | | | | $10^4$ | | | | | |
|---|---|---|---|---|---|---|---|---|---|---|---|---|
| | CPE | | Day 7 | | Day 14 | | CPE | | Day 7 | | Day 14 | |
| Concentration of substance ($\mu$M) | Day 5 | Day 7 | p24 ($\mu$g/ml) | Percentage Inhibition | p24 ($\mu$g/ml) | Percentage Inhibition | Day 4 | Day 7 | p24 ($\mu$g/ml) | Percentage Inhibition | p24 ($\mu$g/ml) | Percentage Inhibition |
| 0 | – | ++++ | – | | 0.25 | | ++ | ++++ | 0.21 | | 0.33 | |
| 0.063 | nt | – | – | N.A. | – | 100 | nt | – | – | 100 | – | 100 |
| 0.125 | nt | – | – | N.A. | – | 100 | nt | – | – | 100 | – | 100 |
| 0.25 | nt | – | – | N.A. | – | 100 | nt | – | – | 100 | – | 100 |
| 0.5 | nt | – | – | N.A. | – | 100 | nt | – | – | 100 | – | 100 |

FIG. 21

Assay: Effect of a protease inhibitor on HIV-1 infection in vitro

Table 19

| Primary HIV-1 isolate HIV$_{Ams}$ 55 | | | | | | | |
|---|---|---|---|---|---|---|---|
| Inoculum (TCID$_{50}$/ml): | | | $10^4$ | | | | |
| Fractions | CPE | | Day 7 | | Day 14 | | |
| | Day 5 | Day 7 | p24 (μg/ml) | Percentage Inhibition | p24 (μg/ml) | Percentage Inhibition | |
| Control | ++++ | ++++ | 0.09 | | 0.57 | | |
| α (0.067 μM) | − | − | 0 | 100 | 0 | 100 | |
| γ (0.5 μM) | − | − | 0 | 100 | 0 | 100 | |
| δ (0.17 μM) | − | − | 0 | 100 | 0 | 100 | |

☐ = not applicable

Assay: Effect of a protease inhibitor on HIV-1 infection in vitro

Table 20

| Primary HIV-1 isolate HIV$_{Ams}$ 37 | | | | | | | | |
|---|---|---|---|---|---|---|---|---|
| Inoculum (TCID$_{50}$/ml): | $10^4$ | | | | | | | |
| Fractions | CPE | | | Day 7 | | Day 14 | | |
| | Day 5 | Day 7 | | p24 (μg/ml) | Percentage Inhibition | p24 (μg/ml) | Percentage Inhibition | |
| Control | +++ | ++++ | | 0.01 | ▢ | 0.29 | ▢ | |
| α (0.067 μM) | − | − | | 0 | 100 | 0 | 100 | |
| γ (0.5 μM) | − | − | | 0 | 100 | 0 | 100 | |
| δ (0.17 μM) | − | − | | 0 | 100 | 0 | 100 | |

▢ = not applicable

FIG. 22

Assay: Effect of a protease inhibitor on HIV-1 infection in vitro

Table 21
Subfraction β

| Primary HIV-1 isolate HIV$_{Ams}$$^{37}$ | | | | | | | | | | | | | |
|---|---|---|---|---|---|---|---|---|---|---|---|---|
| Inoculum (TCID$_{50}$/ml): | $10^3$ | | | | | | $10^4$ | | | | | |
| | CPE | | Day 7 | | Day 14 | | CPE | | Day 7 | | Day 14 | |
| Concentration of substance ($\mu$M) | Day 5 | Day 7 | p24 ($\mu$g/ml) | Percentage Inhibition | p24 ($\mu$g/ml) | Percentage Inhibition | Day 4 | Day 7 | p24 ($\mu$g/ml) | Percentage Inhibition | p24 ($\mu$g/ml) | Percentage Inhibition |
| 0 | +++ | +++ | 0.03 | | 0.34 | | ++++ | +++ | 0.05 | | 0.25 | |
| 0.063 | +++ | ++++ | 0.04 | -33 | 0.30 | 12 | ++++ | ++++ | 0.06 | -20 | 0.27 | -8 |
| 0.125 | +++ | ++++ | 0.03 | 0 | 0.09 | 74 | +++ | ++++ | 0.04 | 20 | 0.15 | 40 |
| 0.25 | - | - | 0.01 | 67 | 0.16 | 53 | + | +++ | 0.02 | 60 | 0.10 | 60 |
| 0.5 | - | - | - | 100 | - | 100 | - | - | - | 100 | 0.02 | 92 |

☐ = not applicable

FIG. 23

FIG. 24

Assay: Effect of a protease inhibitor on HIV-1 infection in vitro

Table 22
Subfraction β

| Primary HIV-1 isolate HIV$_{Ams}$55 | | | | | | | | | | | | | |
|---|---|---|---|---|---|---|---|---|---|---|---|---|---|
| Inoculum (TCID$_{50}$/ml): | $10^3$ | | | | | | $10^4$ | | | | | | |
| | CPE | | Day 7 | | Day 14 | | CPE | | Day 7 | | Day 14 | | |
| Concentration of substance (μM) | Day 5 | Day 7 | p24 (μg/ml) | Percentage Inhibition | p24 (μg/ml) | Percentage Inhibition | Day 4 | Day 7 | p24 (μg/ml) | Percentage Inhibition | p24 (μg/ml) | Percentage Inhibition |
| 0 | +++ | ++++ | 0.08 | | 0.48 | | ++++ | ++++ | 0.12 | | 0.43 | |
| 0.063 | +++ | ++++ | 0.08 | 0 | 0.53 | -10 | ++++ | ++++ | 0.11 | 8 | 0.52 | -21 |
| 0.125 | ++++ | ++++ | 0.09 | -12.5 | 0.60 | -25 | ++++ | ++++ | 0.18 | -50 | 0.68 | -58 |
| 0.25 | - | - | 0.04 | 50 | 0.56 | -17 | ++ | ++++ | 0.08 | 33 | 0.54 | -26 |
| 0.5 | - | - | - | 100 | - | 100 | - | +++ | - | 100 | - | 100 |

☐ = not applicable

FIG. 32 PROTON NMR (MAGNIFICATION OF FIG. 31)

FIG. 33 PROTON (MAGNIFICATION OF FIG. 31)

FIG. 34 PROTON (MAGNIFICATION OF FIG. 31)

Figure 35:
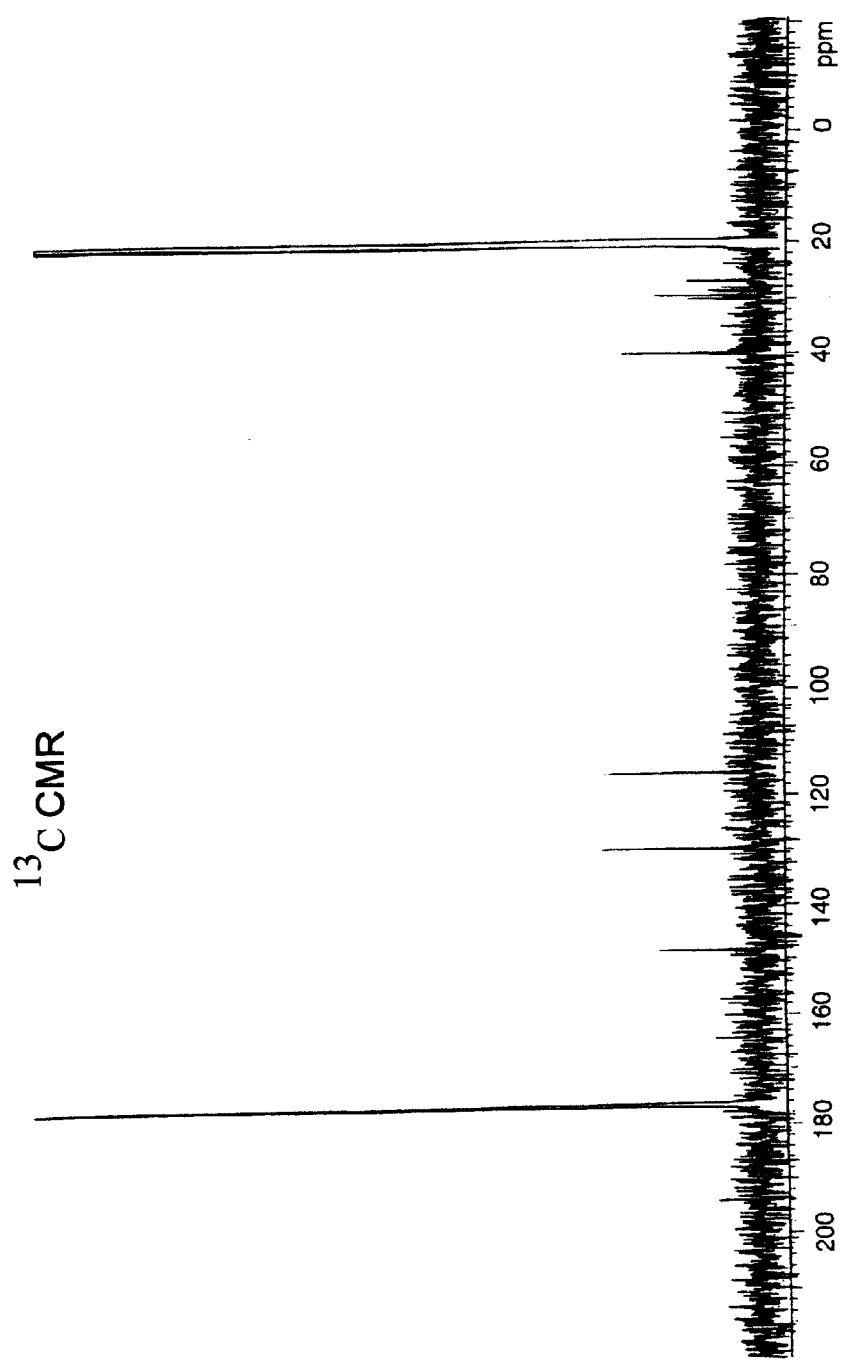
Figure 36:
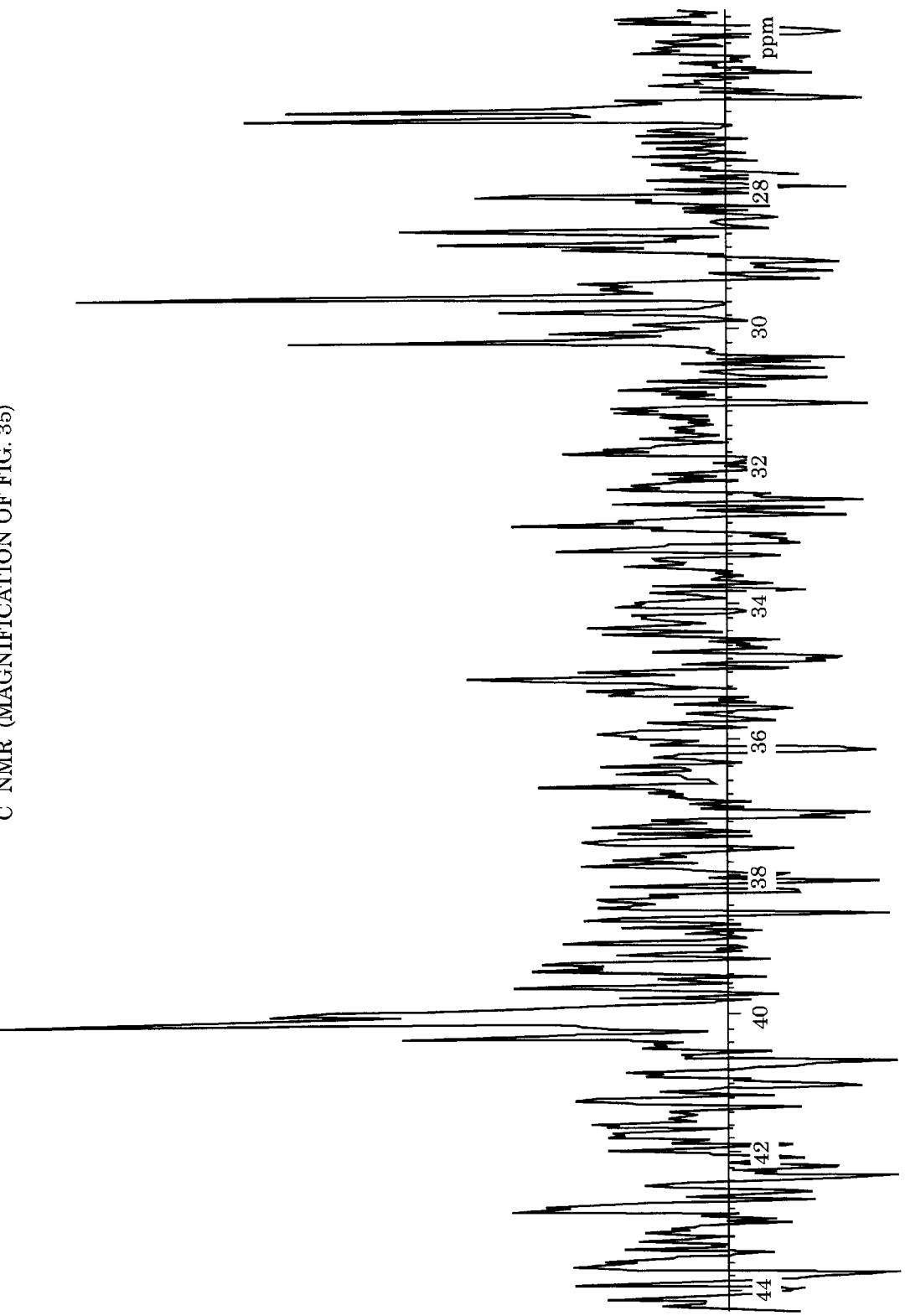
Figure 37:
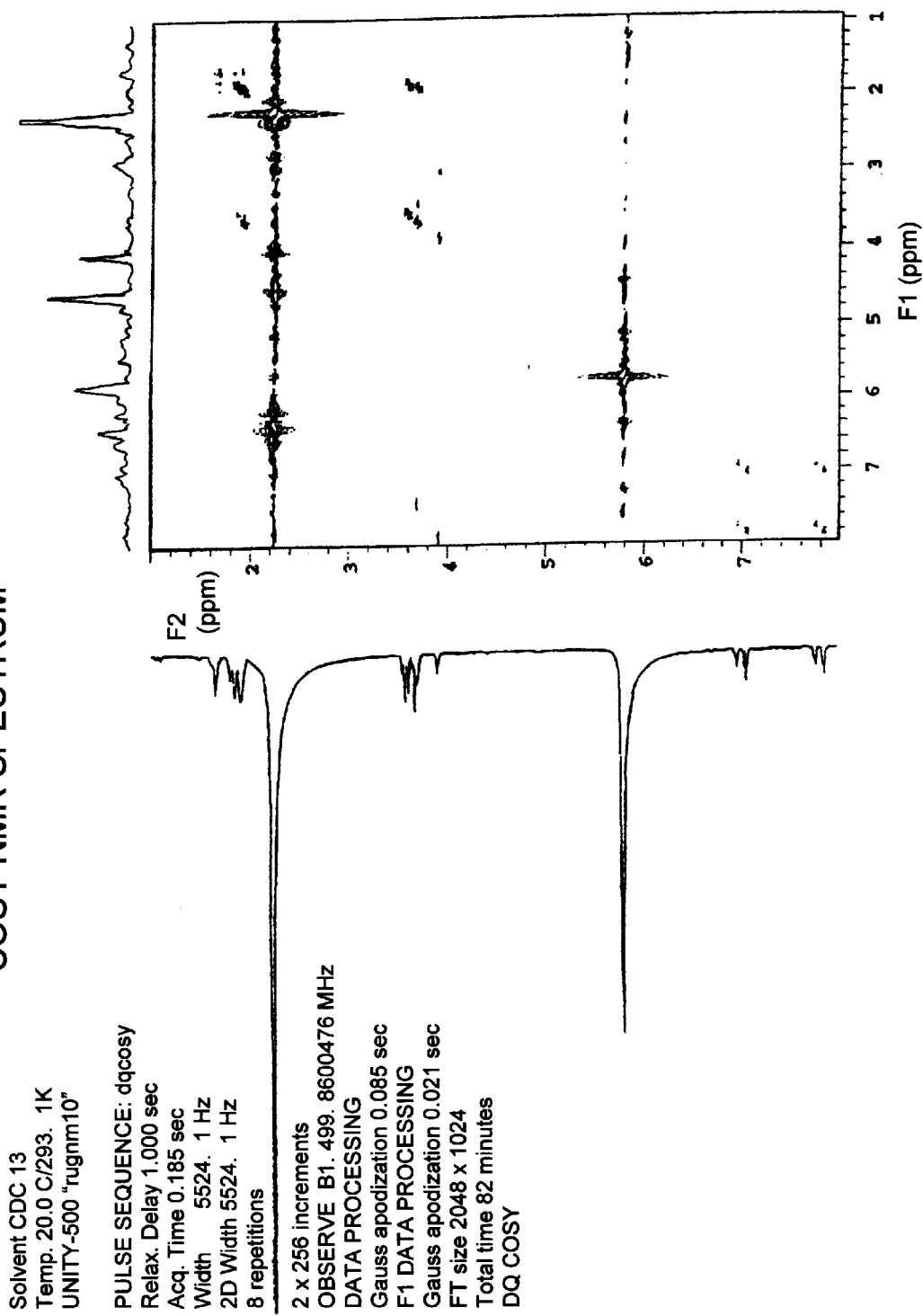
Figure 38:
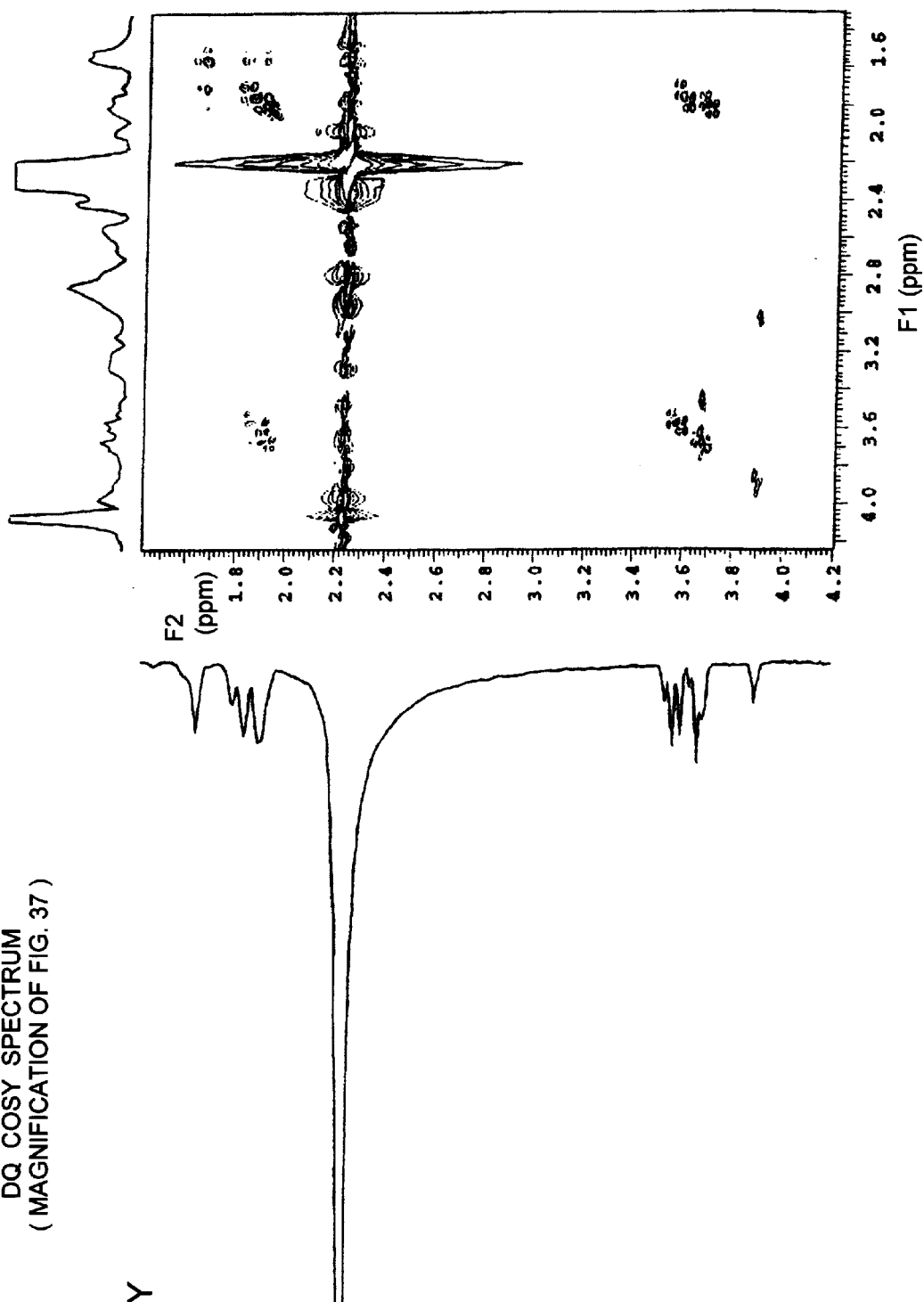
Figure 39:
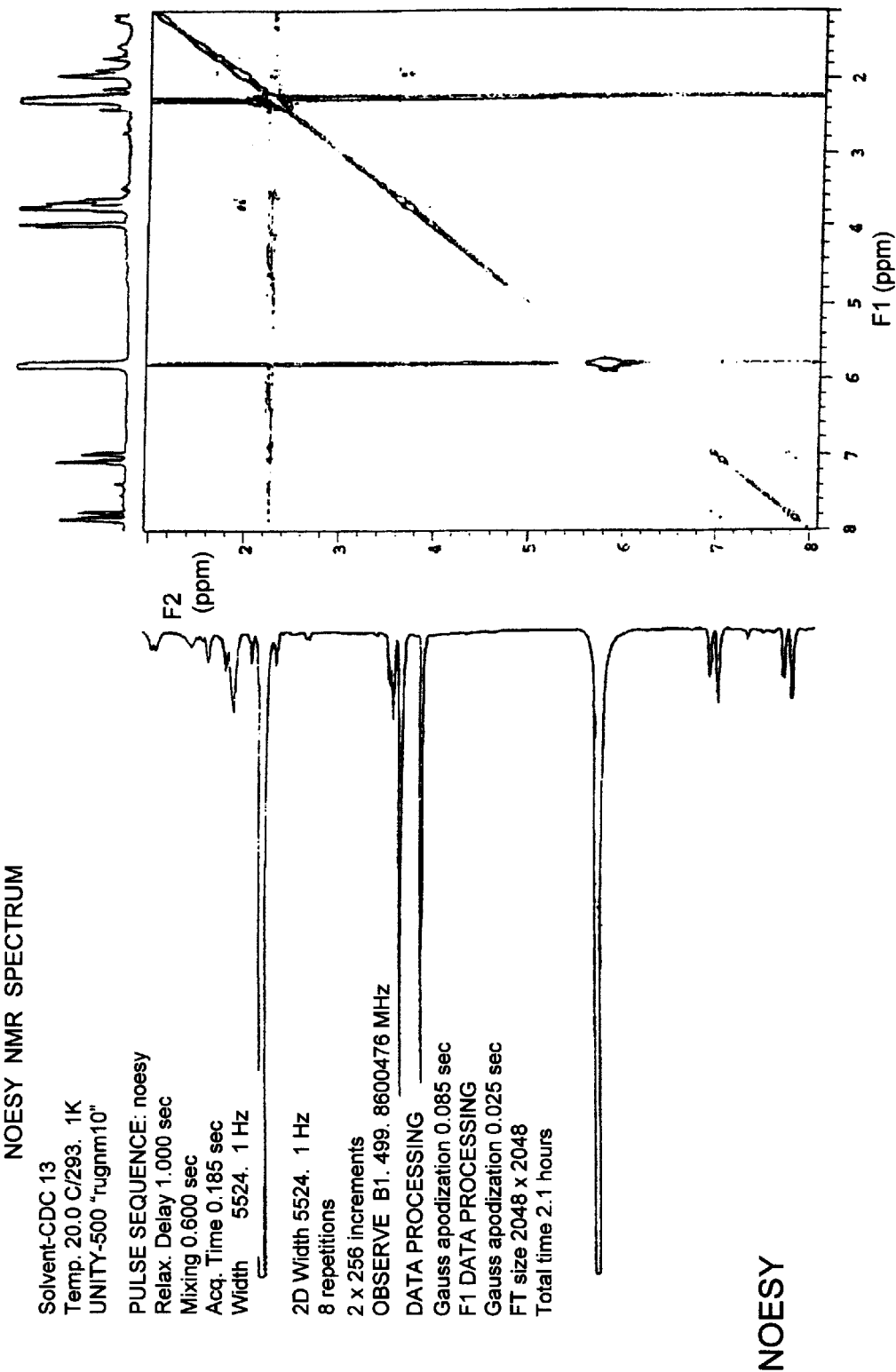
Figure 40:
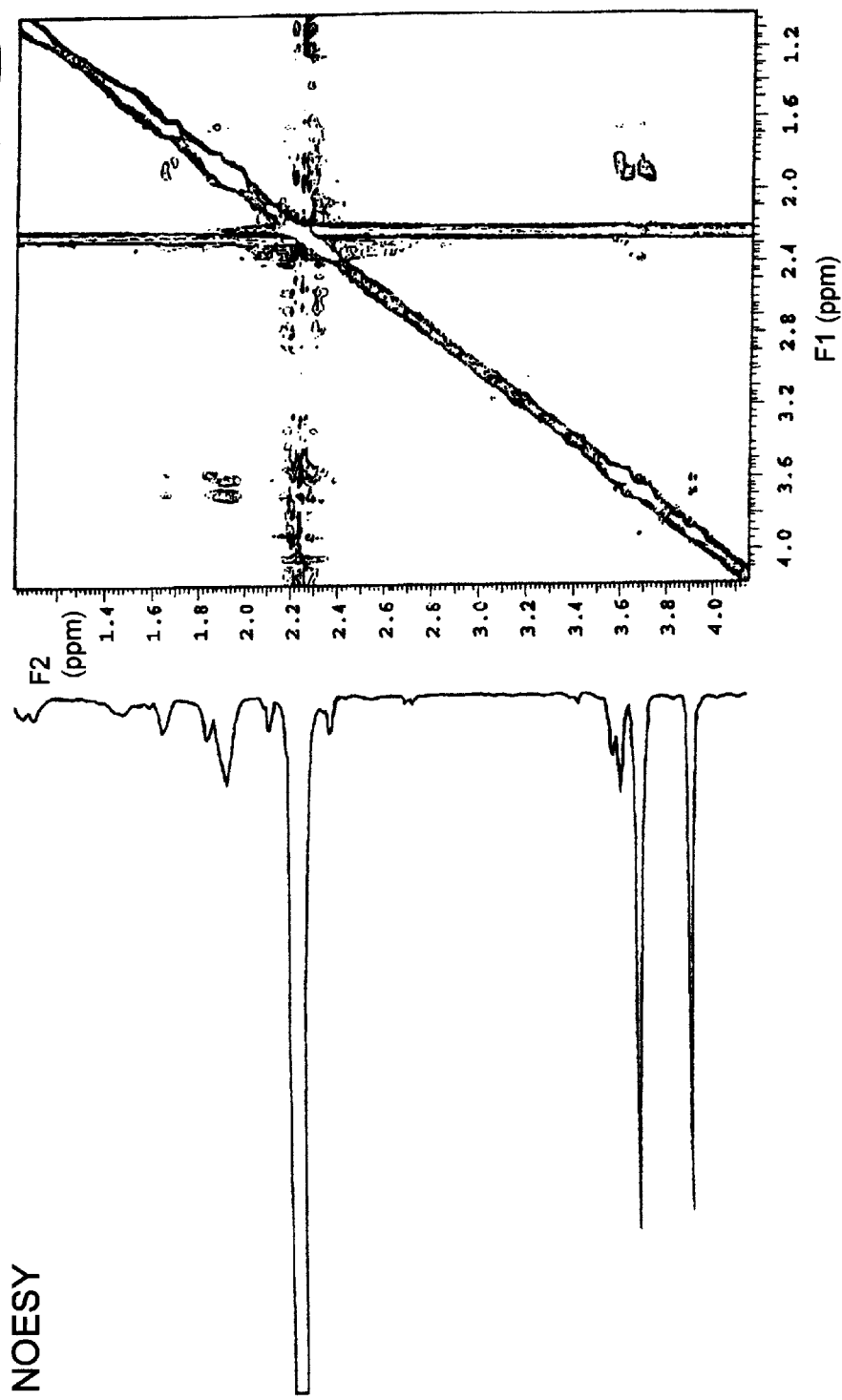
Figure 41:
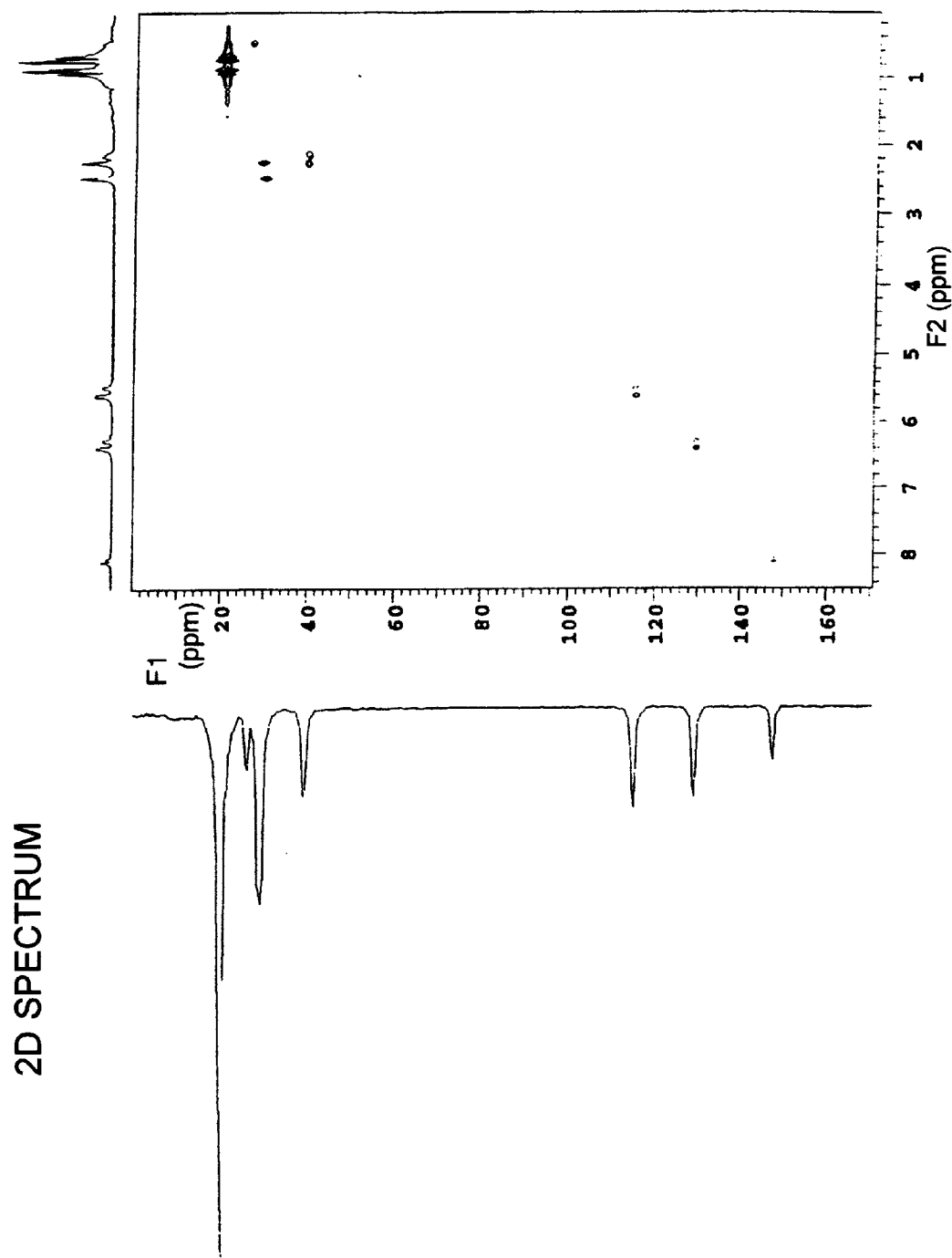
Figure 42:
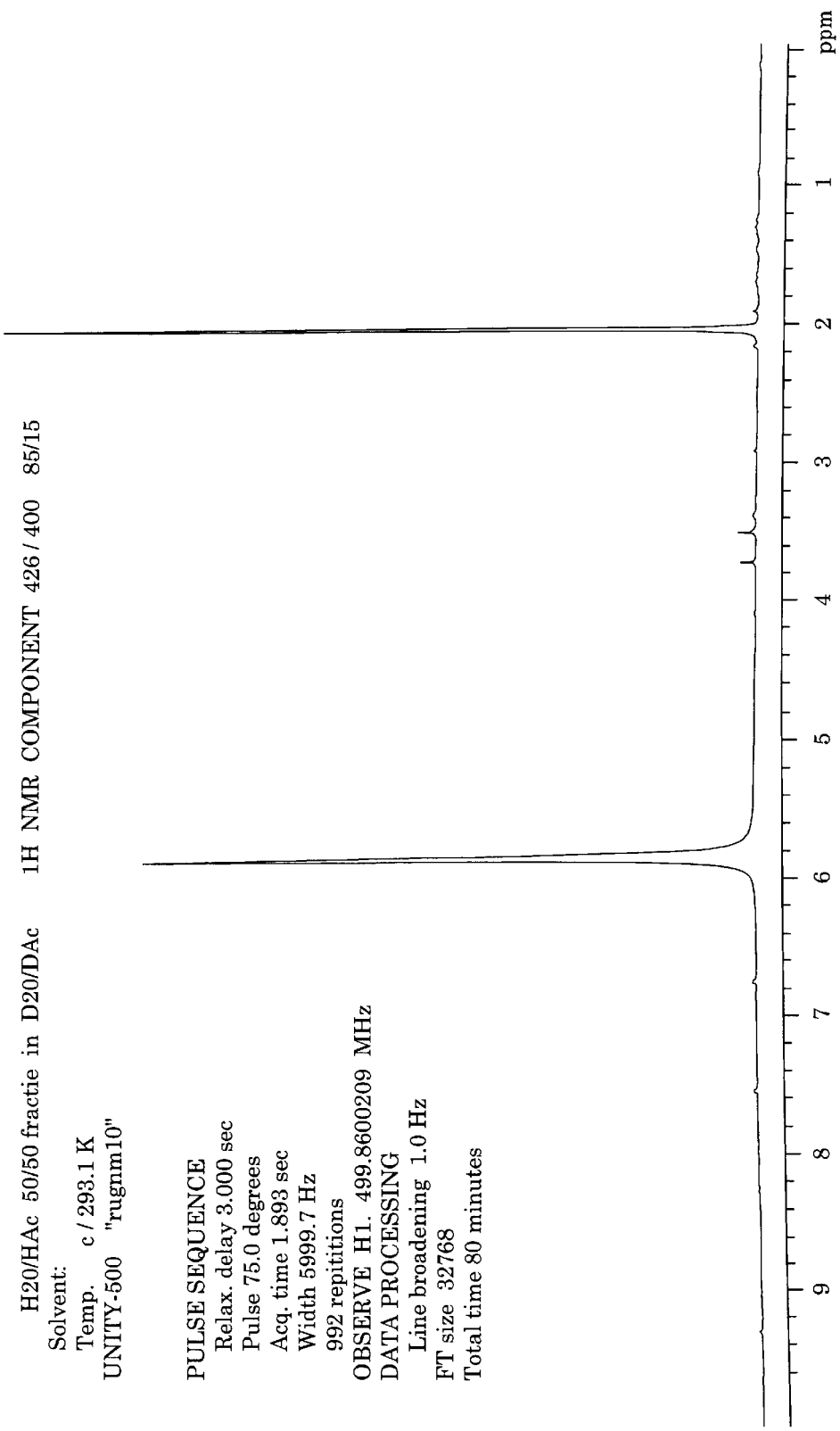

FIG. 35continued exp2 s2pul

| SAMPLE | | DEC. & VT | |
|---|---|---|---|
| date | Oct 6 96 | dn | H1 |
| solvent | d2o | dof | 0 |
| file | /dsk2/org-/vnmrsys/data/jan/-13C_voerman_071096 | dm | y |
| | | dmm | www |
| | | dmf | 9000 |
| ACQUISITION | | dpwr | 37 |
| sfrq | 125.703 | PROCESSING | |
| tn | C13 | lb | 5.00 |
| at | 1.000 | fn | 32768 |
| np | 61120 | math | f |
| sw | 30557.7 | | |
| fb | 16800 | werr | |
| bs | 48 | wexp | |
| pw | 13.5 | wbs | |
| pw | 13.5 | wnt | |
| tpwr | 58 | DISPLAY | |
| d1 | 1.500 | sp | -2617.1 |
| tof | 553.7 | wp | 30557.7 |
| nt | 30000 | vs | 188019 |
| ct | 30000 | sc | 0 |
| alock | n | wc | 250 |
| gain | not used | hzmm | 122.23 |
| FLAGS | | is | 3.11371e+-06 |
| il | n | | |
| in | n | rfl | 5131.2 |
| dp | n | rfp | 2514.1 |
| hs | nn | th | 8 |
| | | ins | 1.000 |
| | | ai  ph | |

DQ COSY SPECTRUM
(MAGNIFICATION OF FIG. 37)

DQ COSY

FIG. 40 NOESY NMR SPECTRUM (MAGNIFICATION OF FIG. 39)

FIG. 41continued

2D SPE exp6 hsqc_g

| SAMPLE | | DEC. & VT | |
|---|---|---|---|
| date | Oct 10 96 | dfrq | 125.702 |
| solvent | cdcl3 | dn | C13 |
| file | exp | dpwr | 58 |
| ACQUISITION | | dof | 652.6 |
| sfrq | 499 | | |
| tn | H1 | dmm | ccp |
| at | 0.127 | dmf | 13889 |
| np | 1344 | dseq | garp1 |
| sw | 5304.3 | dres | 1.0 |
| fb | 3000 | homo | n |
| ss | 2 | temp | 25.0 |
| tpwr | 58 | PROCESSING | |
| pw | 12.0 | sb | 0.117 |
| d1 | 0.800 | sbs | -0.108 |
| d2 | 0.000 | wtfile | |
| tof | 771.2 | proc | ft |
| nt | 128 | fn | 2048 |
| ct | 128 | math | f |
| alock | n | | |
| gain | 28 | werr | |
| FLAGS | | wexp | |
| il | y | wbs | |
| in | n | wnt | |
| dp | y | 2D PROCESSING | |
| hs | nnn | sb1 | 0.010 |
| 2D ACQUISITION | | sbs1 | -0.010 |
| sw1 | 50251.2 | wtfile1 | |
| ni | 512 | proc1 | ft |
| phase | 3 | fn1 | 2048 |
| DISPLAY | | | |
| sp | 24.3 | | |
| wp | 4220.7 | | |
| vs | 1.31083e+-06 | | |
| sc | 6 | | |
| wc | 100 | | |
| hzmm | 23.57 | | |
| is | 689423.49 | | |
| rfl | 3026.9 | | |
| rfp | 2299.4 | | |
| th | 12 | | |
| ins | 1.000 | | |
| ai cdc av | | | |

H2O/HAc 50/50 fractie in D2O/DAc

MAGNIFICATION OF FIG. 43

Figure 43:
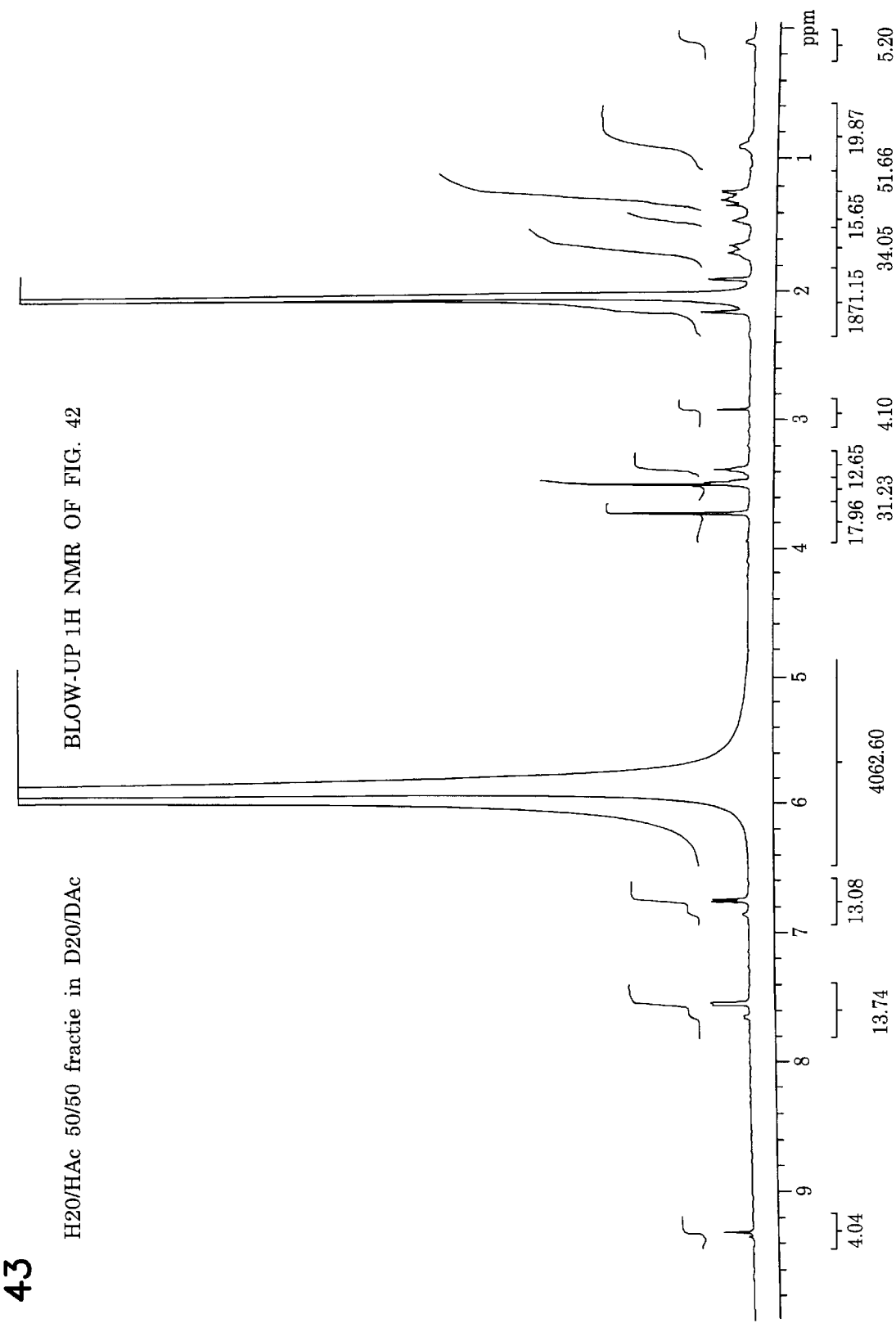
Figure 44:
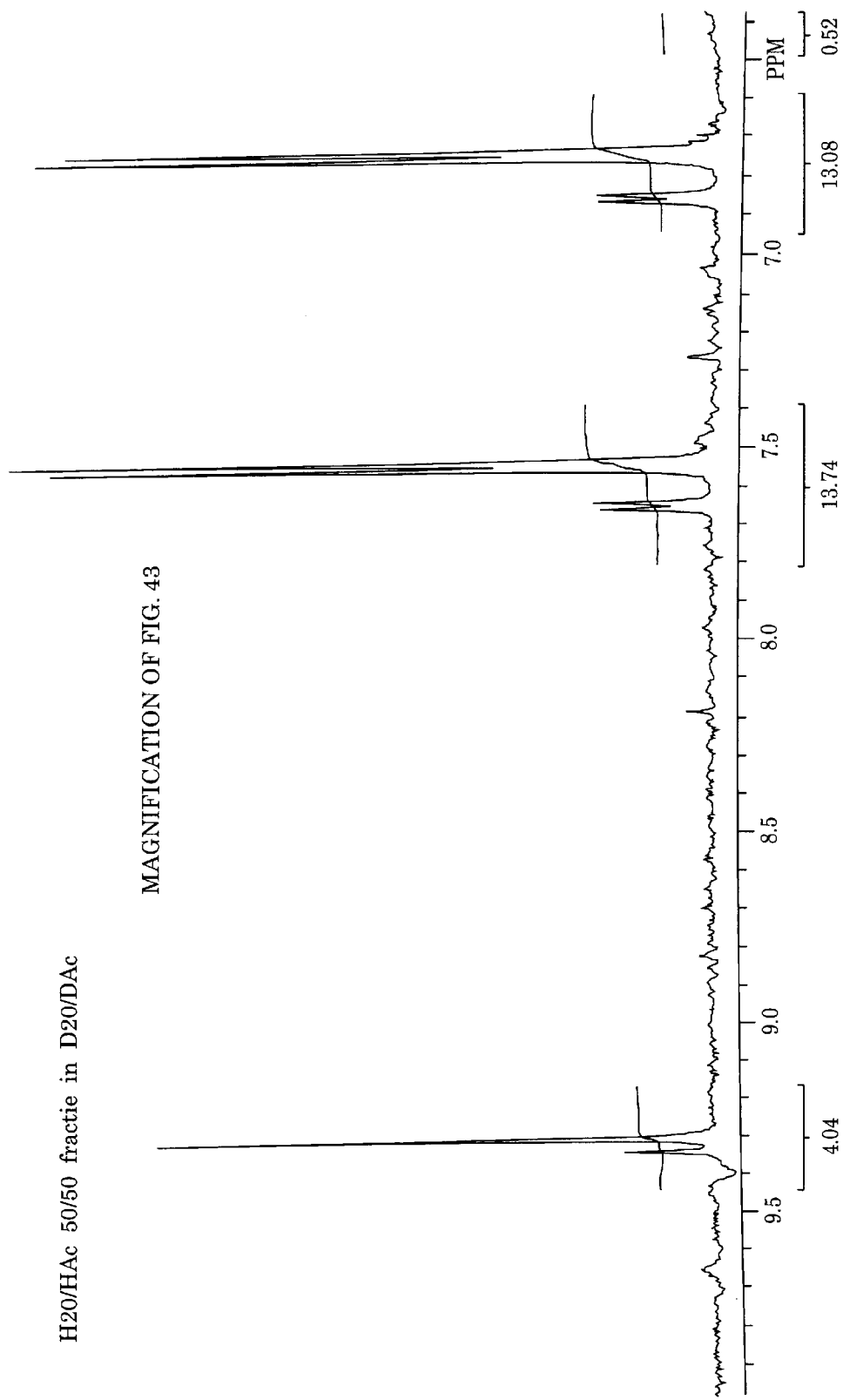
Figure 45:
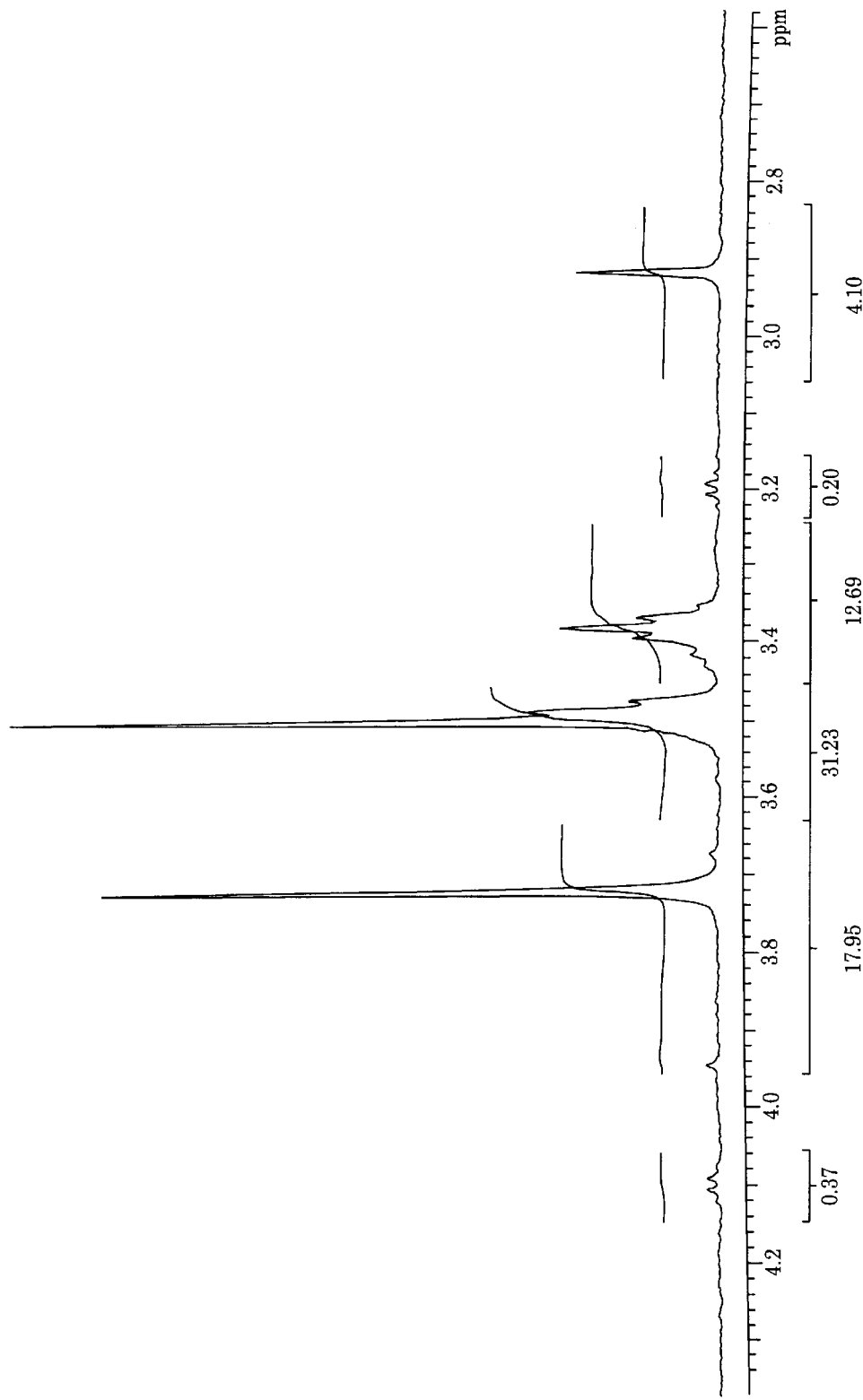
Figure 46:
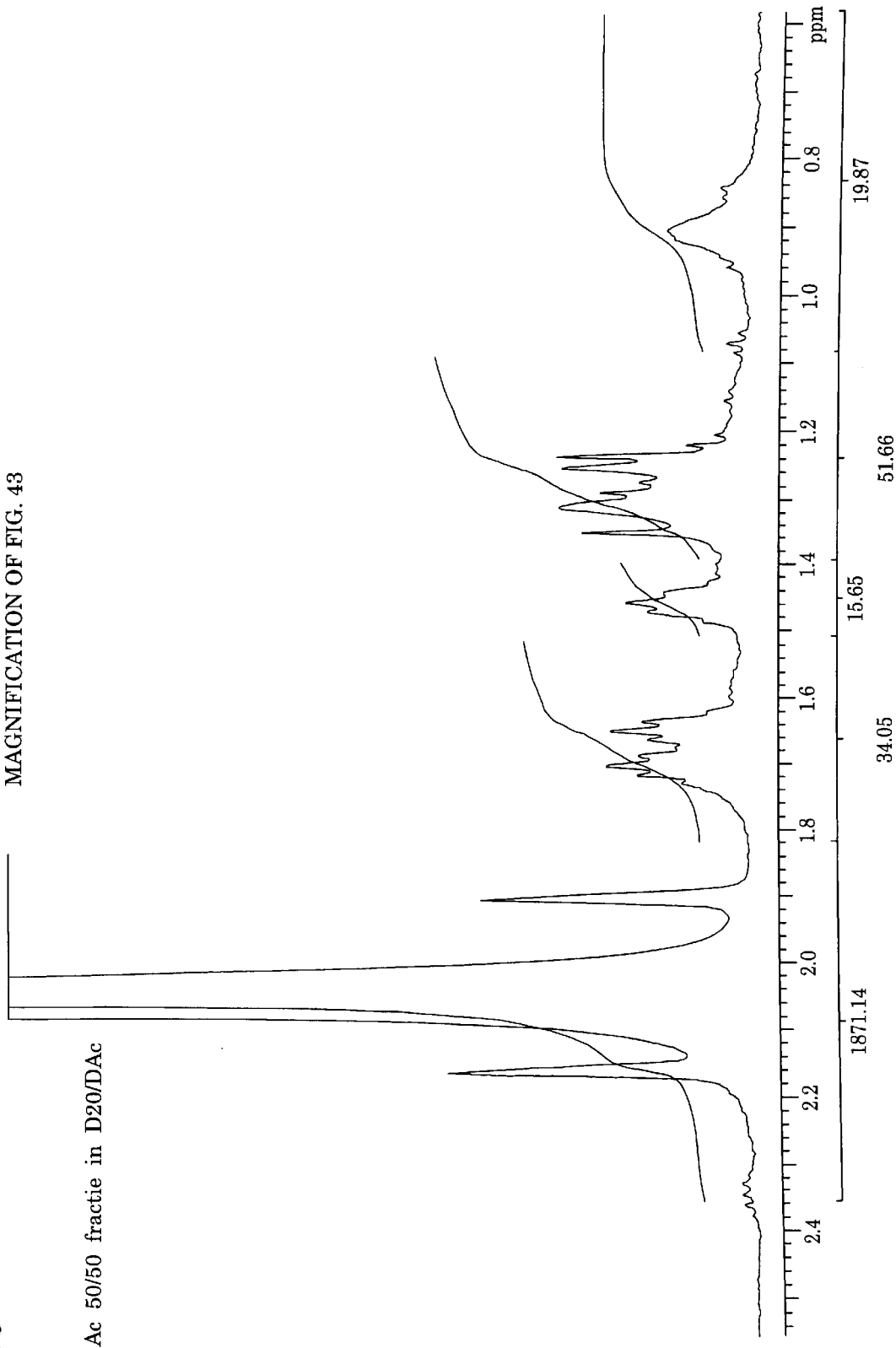

FIG. 45 — MAGNIFICATION OF FIG. 43
H2O/HAc 50/50 fractie in D2O/DAc

FIG. 47 DQ COSY SPECTRUM OF COMPONENTS 426 / 440 85 / 15

FIG. 47continued

V-d2o-DAc
V-d2o-DAc
exp3  relayh

| | SAMPLE | | | DEC. & VT | |
|---|---|---|---|---|---|
| date | | Nov 1 96 | dfrq | | 499.862 |
| solvent | | CDC13 | dn | | H1 |
| file | | exp | dpwr | | 30 |
| | ACQUISITION | | dof | | 0 |
| sfrq | | 499.863 | dm | | n |
| tn | | H1 | dmm | | c |
| at | | 0.171 | dmf | | 200 |
| np | | 2048 | dseq | | |
| sw | | 5999.7 | dres | | 1.0 |
| fb | | 3400 | homo | | n |
| bs | | 32 | temp | | 20.0 |
| ss | | 2 | | PROCESSING | |
| tpwr | | 58 | sb | | 0.086 |
| pw | | 12.0 | sbs | | not used |
| p1 | | 12.0 | wtfile | | |
| d1 | | 1.000 | proc | | ft |
| tof | | 1111.3 | fn | | 2048 |
| nt | | 32 | math | | f |
| ct | | 32 | | | |
| tau | | 0 | werr | | |
| relay | | 0 | wexp | | |
| alock | | n | wbs | | |
| gain | | 30 | wnt | | |
| | FLAGS | | | 2D PROCESSING | |
| il | | n | sb1 | | 0.018 |
| in | | n | sbs1 | | not used |
| dp | | y | wtfile1 | | |
| hs | | nn | proc1 | | ft |
| | 2D ACQUISITION | | fn1 | | 2048 |
| sw1 | | 5999.7 | | | |
| ni | | 256 | | | |
| phase | | 0 | | | |
| | DISPLAY | | | | |
| sp | | -17.5 | | | |
| wp | | 4844.3 | | | |
| vs | | 4502 | | | |
| sc | | 6 | | | |
| wc | | 100 | | | |
| hzmm | | 3.79 | | | |
| is | | 33.57 | | | |
| rfl | | 1120.2 | | | |
| rfp | | 1014.7 | | | |
| th | | 3 | | | |

Figure 47:
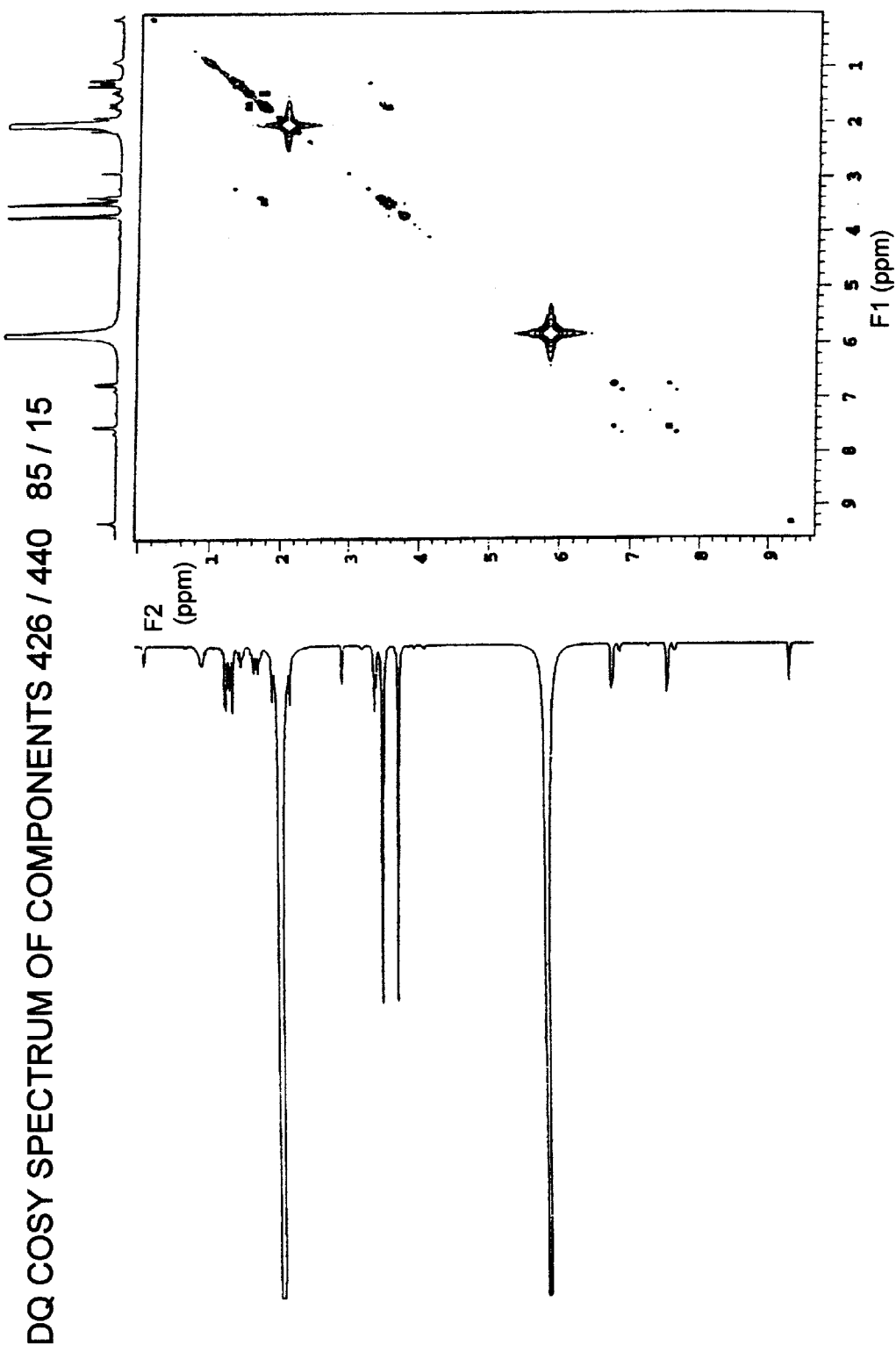
Figure 48:
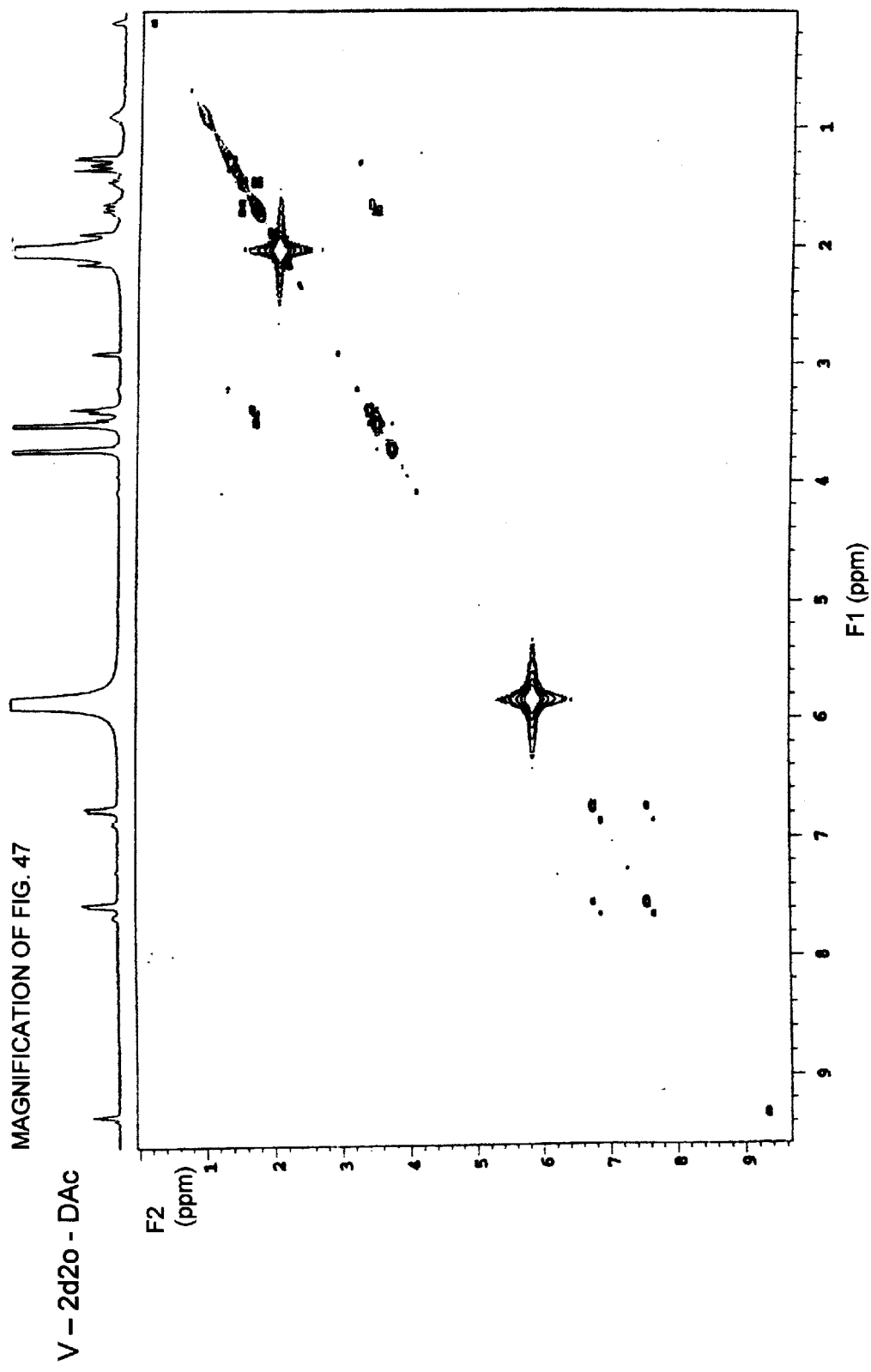

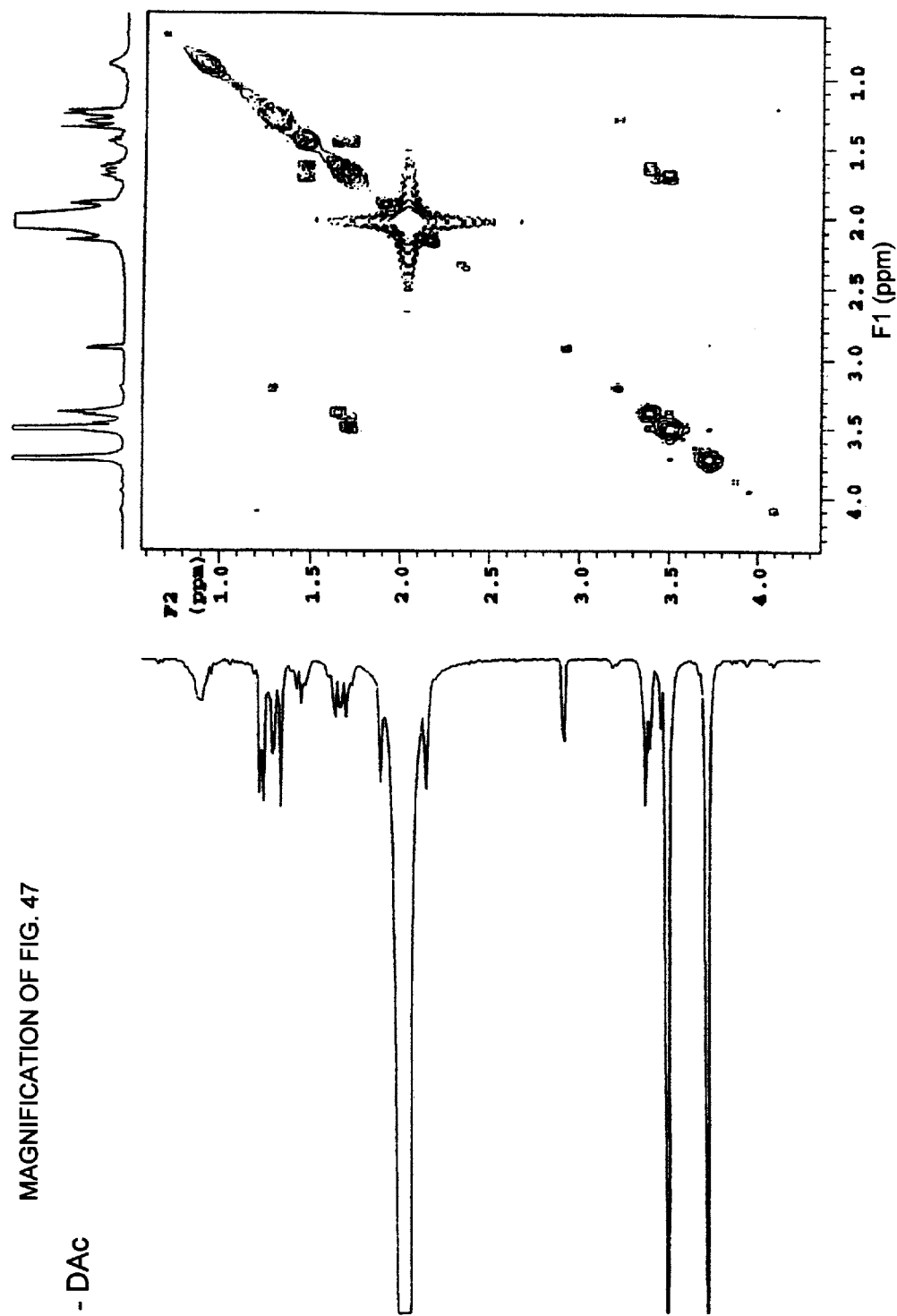
FIG. 49 MAGNIFICATION OF FIG. 47
V – d2o – DAc

ANTI-VIRAL ISOLATES OBTAINABLE FROM LEECHES

The present invention relates to the field of anti-viral compounds, e.g. in the field of immune diseases, particularly acquired immune diseases, more in particular to infections with human immunodeficiency virus.

A new human immunodeficiency with opportunistic infections and malignicies was described in 1981. The causative agent was found to be a retrovirus, Human Immunodeficiency Virus (HIV). The pathogenesis of the disease begins with the alteration and eventual depletion of T4 lymphocyte cells, leading to a progressive destruction of the immune system.

HIV is a retrovirus, consisting of a capsulated RNA-genome surrounded by a double-layer core-membrane. An early finding was the variation of nucleotide sequences of certain parts of the genome, especially in the envelop gene (Shaw, et al, 1986).

the gag and pol genes of HIV are translated as two polyproteins (Pr55gag and Pr160gag-pol) (Jacks, et al, 1988). These are subsequently cleaved by the action of a virus-encoded protease into four structural gag proteins of the virion core (p17, p24, p7 and p6) (Veronese, F D., et al., 1987), and the pol-encoded enzymes essential for retrovirus replication (protease, reverse transcriptase, ribonuclease H., and endonuclease).

Viral core-glycoprotein precursor gp160 component gp120 binds to CD-4, a cellular receptor of the susceptible T-cell subset with high affinity (Berman, et al, 1989). Therefore, viral recognition and fusion of CD-4 with gp120 is a pivotal occurrence in the infection cycle. It should be noted however, that other factors may play a role as well: Neutralizing antibodies to the V3 loop of gp120 prevent infection even though they do not inhibit binding to CD4 (Rusche, et al, 1985), and Productive infection of monocytes, in absence of proliferation and DNA synthesis of T lymphocytes, can occur and serve as relative long-lived reservoirs of virus (Weinberg, et al, 1991).

Drug development against HIV infection sofar has aimed at preventing fusion between the CD4 membrane protein and viral gp120 and thus preventing mediation of HIV entry into the cytoplasm of T4 lymphocytes. Vaccination with recombinant gp120 (rgp120) led to protection of chimpansees from HIV infection (Berman P W., et al, 1990). Cytopathic fusion of CD-4 cells (syncytia) occurs on expression of gp120 at the plasma membrane. Soluble CD4 blocks secretion and surface expression of gp120 prevents such cell fusion (Buonocore & Rose, 1990).

Other attempts to develop drugs against infection with HIV have so far focused on the inhibition of HIV reverse transcriptase (RT) and HIV protease. RT is the target of AZT, the first anti-HIV drug in clinical use. A TIBO derivative RS2150 was found to inhibit 50% of HIV RT at a concentration of 3.1 $\mu$M and 4.9 $\mu$M respectively for different viral strains (Pauwels, et al, 1990).

HIV protease inhibition is for example disclosed in EP 541168, U.S. Pat. No. 5,196,438, and in WO092/08701. Inhibition of proteases results in the production of non-infectious virus particles and unprocessed gag and gag-pol precursor proteins (Kohn, et al, 1988: Loeb, et al, 1990). Recent disclosures aiming at inhibition of either HIV protease or HIV RT in patent literature are: WO 95/20384, WO 95/16688, WO94/06454, EP 0666755, EP 0666842, WO 95/14011, and many more.

A range of antigenically distinct HIVs have been isolated, (even within one individual) causing a major problem in drug development against HIV. Moreover, many drugs which seem promising in vitro suffer from the fact that the virus is capable of escaping their effect in vivo by quick mutagenesis.

The present invention provides a new group of substances capable of inhibiting Human Immunodeficiency Virus, which can thus be used to prevent or combat HIV infection and/or AIDS.

During laboratory testing of a newly discovered range of protease inhibitors from leeches (see EP 94117053.2 and EP 95103637.5) very potent elastase-, chymotrypsin-, trypsin-, plasmin- and thrombin inhibitors were defined. Since the proteolytic cleavage of the gag and env precursors in the replication cycle of HIV is an important step, it was investigated if the newly described inhibitors would have any effect on such virus replication. Development of inhibitors is a rationale in anti-viral drug development. The aim of such study was to evaluate the antiviral capacity of the protease inhibitors, which were the subject of EP 94117053.2 and EP 95103637.5, on primary cells.

It was concluded in the above-mentioned patent applications, that anti-viral capacity was indeed present in the described inhibitors. However, it has now been surprisingly found, that a farm more potent anti-viral substance or group of substances resided in the original leech and leech-head ethylalcoholic extractions. These substances or groups of substances containing such surprising activity are the subject of the present invention. We have purified and characterized the substances.

The present invention thus provides an isolate or compound having inhibitory activity towards virusses, e.g. towards a human immunodeficiency virus, obtainable from leeches or organisms associated with leeches of the phylum uniramia by solvent extraction techniques and having a molecular weight of about 300–600, preferably about 400–500 Dalton. Preferably the compound is obtainable from the subclass of euhirudinae, in particular it is obtainable from the suborder hirudiniformes, preferably the order of arhynchobelidae. Most preferred are compounds which are obtainable from the family hirudinidae, in particular those which are obtainable from the genus Limnatis, in particular the species *L. nilotica*. *L. nilotica* (Savigny, 1820, as following from Autrum 1936) is described as a "nasal leech" or horse leech (Mouquin-Tandon 1846). It was found to be present in the whole littoral area of the Mediterranean (Harant, 1928; Jarry, 1959). It lives in spring fountains and "oueds", and feeds on cattle, dogs and man (Blaise, 1874/5; Neveu & Lemaire, 1938; Turner, 1969; Keegan, et al, 1970).

Amazingly, the feeding habits of this leech differ from other haemotophaguos leeches. It remains attached to its host (nasal—and laryngeal cavity) for prolonged periods (weeks to months). The animal feeds on its host repeatedly. We have observed that drinking cattle were infected with these leeches, which did not drop off while the cattle are drinking water. Only thick, fat, adult-size leeches do drop off at such occasions. Therefore, it is clear that this species of leech is mostly free of antigenic or immunogenic substances in its mucus or salivary gland productions. Reports of host animals dying from this species of leech mention anemia as the one common cause, but no direct antigenic effect has been described to our knowledge. In one aspect the invention thus provides compounds having HIV inhibiting activity obtainable from the leech Limnatis nilotica or fragments of derivatives of such compounds having similar activity.

Such compounds can be derived from all body parts and secretions of the leech, including saliva- and gut-, intestinal- and skin secretions and mucus.

The most suitable source for the compounds according to the invention is probably solvent extraction of the heads of the leeches, or compounds associated with these heads. As may be understood it is also possible that the actual source of the compounds according to the invention may not be the leech itself, but it may be derived from a leech associated material or organism, such as a bacterium.

These compounds obtainable from for instance a bacterium associated with the leeches are also a part of the present invention. The requirement is that they are obtainable by solvent extraction techniques when applied to the leeches, that they have the characteristics as disclosed herein, of which the anti-viral activity, and esp. the HIV-inhibition, is the most important characteristic. The compounds may even be the result of interaction between leech derived and other materials.

The present invention also provides a method for obtaining a compound having human immunodeficiency virus inhibiting activity comprising dehydrating leech tissue, preferably leech heads, or secretions preferably saliva, optionally lyophilizing the resulting extract, suspending the lyophilized material in an aqueous solution, centrifuging the material to obtain a pellet, loading resulting supernatant on a size fractionation column, eluting the column with an aqueous solution, collecting fractions of the eluted material, testing the fractions for human immunodeficiency virus inhibiting activity and collecting the active fractions.

Isolates obtained by the process of the invention undoubtedly posses an anti-viral activity. Without being wished to be bound to a theory, it is assumed—e.g. on the basis on the analytical test data herein-below—that the anti-viral activity can be attributed to an active ingredient having a general formula $Ar^1$-spacer-$Ar^2$, wherein $Ar^1$ is an aromatic six-ring, which preferably is para-substituted, e.g. with a hydroxyl group or an amino group, which siz-ring can also be substituted at the other positions with e.g. $C_{1-4}$ alkyl groups, and halogens; wherein the spacer contains a $C_{3-8}$ alkylene group coupled through a hydrophilic group, such as an amido group, to $Ar^1$; and wherein $Ar^2$ is a heteroaromatic 2-ringsystem based on carbon and nitrogen atoms (the 2-ringsystem having 9 or 10 atoms (purine- or naphthene-like ringsystems)), which ringsystem can be substituted with e.g. $C_{3-8}$ alkyl groups, hydroxy groups, amino groups, halogens etc; as well as addition salts, solvates and dimers of these isolates.

It can however not be ruled out that other ingredients of the isolates obtained are the potent inhibitors or anti-viral compounds or attribute to the activity shown.

Preferably, such a method further comprises subjecting active fractions to a further separation step, preferably using an HPLC column. The isolates or compounds obtainable by these methods which have been isolated sofar have a low molecular weight. When testing these compounds for their inhibitory activity, it was found that the compounds or mixtures of compounds according to the invention have anti-viral activity in general, e.g. human immunodeficiency virus inhibitory activity in the micromolar range. It is e.g. found that the isolate completely inhibits human immunodeficiency virus induced syncytium formation of p24 production at 0.5 $\mu$M, preferably 0.17 $\mu$M, most preferably 0.067 $\mu$M concentrations. The invention further provides the use of these compounds or mixtures in preventing or combating infections with HIV an/or AIDS and thus also provides a pharmaceutical composition comprising at least one compound according to the invention and a suitable vehicle for administration. Based on the kind and amount of activity of the compounds and the amounts tolerated, which can be determined in animal studies using rising doses the person skilled in the art will be able to develop these pharmaceutical formulations.

Administration may be accomplished in any suitable manner, although for some compounds in systemic applications parenteral routes may be preferred. Dosages for these substances can be taken from the literature and designed on the basis of specific activities of the substances, the molecular weight of these substances, the weight of the subject to be treated, the kind of application etc. Dosage will usually lie between 0.1 $\mu$g/kg and 10 mg/kg bodyweight. Suitable excipients are well known in the art and range from water for injection to carrier proteins such as serum albumin for e.g. lyophilized preparations and inert substances such as mannitol, cellulose and dextran for tablets or granulates. The easiest way is of course simply providing the compounds in sterile water (or saline) for injection.)

Included in the invention are also mutations, isoforms, derivatives, such as salts and solvates, fragments or even peptidomimetics or other mimicks, and anti-idiotype or catalytic antibodies of the HIV (replication) inhibiting substances.

Synthetic manufacture of the invented substances, mutations, isoforms, derivatives, and fragments is also included in this invention, as are intermediates which are useful for obtaining the compounds according to the invention.

Experimental

During research work with *L. nilotica* derived protease inhibitors, it was surprisingly observed, that, next to HIV replication inhibition activity of the protease inhibitors mentioned hereinbefore, another fraction, obtained from *L. nilotica* heads ethanol extracts, was far more potent. This group of substances is named SILIAVIR in the present description.

In a biologic test system with primary cells, which is described further hereinbelow, it was concluded, that whole leech's head'extract showed a dose dependent inhibition of HIV replication in two separate HIV isolates, being almost complete at a concentration of 0.5 $\mu$M (see Table 1 and Table 2 of FIG. 1).

Further isolation and purification methods in steps, finally led to a group of active compounds also called substances herein, having a molecular weight of around 05. kD, which show e.g. HIV replication inhibition at 100% at such low concentrations as 0.06 $\mu$M.

The biological effects as measured are not yet related to one of the know strategies in drug development against viruses, in particular retroviruses, and more specifically against HIV. However, any of these well-known strategies could be involved (e.g. RT inhibition, sCD4, gp120 substitute, HIV protease inhibition). Other possible ways of activation are not excluded) for example, but not limited to: effects on the cells, as well as effects on the challenging virus, or the combination of the two), and are being researched.

The present invention reveals the isolation and purification steps, in combination with the biologic test system in primary cells, leading to this group of new and unique substances, having the specific activities as described. Applicant specifically intends that this substances Siliavir as invented, and described herein, includes such substance however produce, be it through sequential and block synthesis, or through gene cloning and expression, or by whatever other synthetic mechanism.

Description of Biologic testing and of Isolation and Purification.

A. Biologic test system
Peripheral blood mononuclear cells

Phytohaemagglutinin (PHA) stimulate PBMC from healthy donors were inoculated with two different HIV isolates (HIVAms 37 and HIVAms 55). After a two-hour exposure to the HIV isolates, the inoculum was removed and serial concentrations Siliavir were added to the cultures. Medium was changed twice a week, fresh PMA-stimulated PBMC were added every week. Buffy-coats are routinely screened for viral contaminants and used only when negative for these contaminants. Virus production in the cultures was monitored with a p24-capture ELISA, detecting p24core protein of HIV. Cultures were also monitored for the occurrence of cytopathic effects (syncytium formation).

Culture medium

During the first two days after isolation of the cells, primary peripheral blood leukocytes were cultured in Iscove's Modified Dulbecco's Medium (IMDM), supplemented with 10% foetal Calf serum (FCS), polybrene (5 $\mu$g/ml), phytohaemagglutinin (5 $\mu$g/ml), penicillin (100 IU/ml) and streptomycin (100 IU/ml). The T-cell blasts were then further cultured in IMDM supplemented with 10% FCS, polybrene (5 $\mu$g/ml), recombinant IL-2 (10 IU/ml), penicillin (100 IU/ml) and streptomycin (100 IU/ml).

Viruses

High titre inocula of two primary syncytium inducing HIV isolates were prepared. Titers of stock were determined in a TCID50 assay.

During the first two days after isolation of the cells, primary peripheral blood leukocytes were cultured in Iscove's Modified Dulbecco's Medium (IMDM), supplemented with 10% foetal Calf serum (FCS), polybrene (5 $\mu$g/ml), phytohaemagglutinin (5 $\mu$g/ml), penicillin (100 IU/ml) and streptomycin (100 IU/ml). The T-cell blasts were then further cultured in IMDM supplemented with 10% FCS, polybrene (5 $\mu$g/ml), recombinant IL-2 (10 IU/ml), penicillin (100 IU/ml) and streptomycin (100 IU/ml).

Experimental design

A total of $10^7$ PHA-stimulated PBMC were inoculated with $10^4$ TCID50/ml of the primary HIV isolates in a volume of 1 ml for 2 hours at 37° C. After 2 hours, cells were washed in a total volume of 30 ml. After centrifugation, supernatant was discarded to remove non-absorbed virus. Cells were subsequently resuspended to a final concentration of $10^6$/ml. From each cell suspension 100 $\mu$l aliquots containing $10^5$ cells were transferred to wells of a 96 well tissue culture plate. Dilutions of fractions of Siliavir were made from stock solutions of 1 $\mu$M, in culture medium in such a way that after addition of 50 $\mu$l to each well the final concentrations in the wells was 0.063, 0.125 $\mu$M, 0.25 $\mu$M, and 0.5 $\mu$M. Cells that received only medium served as untreated control cultures. Each concentration was analyzed in four fold. Cells were cultured in a humidified atmosphere at 37° C., 5% $CO_2$. Addition of $10^5$ fresh PHA stimulated PBMC and medium was performed on day 7. In parallel, a new dose of the same concentrations of Siliavir was added.

Controls

On days 4 and 7, cultures were analyzed for any HIV-induced cytopathic effect as reflected by the presence of syncytia. At days 7, and 14, 30 $\mu$l of the culture supernatant was harvested to analyze the presence of p24 antigen in a p-24-antigen-capture-ELISA. For this, twice a week, 30 $\mu$l aliquots were harvested from the cultures and inactivated by the addition of 30 $\mu$l 0.2% Triton-X-100. 15 $\mu$l of this mixture was added to wells of a 96 well ELISA plate coated for 2 hours at 37° C. with an anti-p24 antibody shown to recognize all HIV isolates. Antigen was allowed to bind during 2 hours at 37° C. Bound p24 was detected with immunoglobulin (90' at 37° C.). Then, substrate (TMB) was added and after 20', the reaction was stopped by the addition of $H_2SO_4$.

Results are presented in Tables 1 and 2 (FIG. 1). The tables should be read with the following in mind.

Calculation of results

For the calculation of the percentage inhibition the following formula was used $$\text{Percentage inhibition} = \frac{p24 \text{ production in untreated cultures} - p24 \text{ production in cultures exposed to substance}}{p24 \text{ production in untreated cultures}} \times 100\%$$

Criteria

Cultures were considered positive if:
Syncytia formation was observed on at least one occasion (cultures were examined twice a week) in combination with an elevated p24 antigen content in the supernatant on at least one occasion.

Syncytium score:
- − no syncytia observed in any of the four replicate cultures,
- ± syncytia observed in one out of four replicate cultures
- + syncytia observed in two out of four replicate cultures
- ++ syncytia observed in three out of four replicate cultures
- +++ syncytia observed in four out of four replicate cultures

Results

HIV-1 induced cytopathic effects (CPE), production of p24 antigen, and calculated percentages inhibition are demonstrated in Tables 3 and 4 for substance 1 and in Tables 1 and 2 for substance 3.

Data for p24 production represent the mean of four replicate cultures

Cultures inoculated with $10^2$ $TCID_{to}$ remained negative for virus production.

Substance three, mentioned in these tables, represents whole leech heads extract. The extract processing, purification and isolation are described below.

Each time a new purification step takes place (see below), the described biologic test system is used as an "affinity test-system" to further narrow the active substances from the extract fraction.

B. Methods for isolation and purification

A total of 15 g of cut heads from frozen *Limnatis nilotica* were dehydrated in 94% ethylalcohol at room temperature. Three changes of a total of 134 ml, after which 400 ml destilled water was added, and the extract was subsequently lyophilized in vials. A total of ca. 90 mg of lyophilized material was assembled. (One can also use, as an alternative, chopped heads of these leeches, or use activated mucus secretions from live leeches, by immersing them for instance for 10 minutes in 4% ethylalcohol at room temperature).

The lyophilized material (ca. 90 mg) was first suspended in 4.55 ml destilled water. Thereafter, three portions of 4.55 ml of destilled water were added. 50% of this suspension (9.1 ml) was further diluted with 30 ml destilled water, the other 50% stored at −20° C. the suspension was divided over two centrifugation tubes and centrifuged. The pellet was stored at −20° C. 50% of the supernatant was also stored at −20° C. The other 50% of the supernatant was loaded on a Sephadex G-75 column (length 180 cm, diameter 1.85 cm). Eluens is distilled water, fraction size: ca. 4–7 ml; flow adjusted at ca. 0.5 to 1 ml/min. A total of 149 fractions were sampled and absorption was measured at 214 nm. The flow at the column reduced from its initial setting of 1 ml/min to ca. 0.5 ml/min and the fraction size diminished from initial 7 ml to 4 ml (fraction 1 to 25: ca. 7 ml; fraction 26 to 29: ca. 6 ml; fraction 30 to 79; ca. 5 ml and fraction 80–149; ca. 4 ml). A slight opalescense was visible in fractions 19 to 24, while a precipitation was visible in fractions 95 to 108. Based on the absorption diagram (FIG. 2) and SDS-PAGE (FIG. 3) the following pools for further trials were made:

fraction 16 to 29 (ca. 83 ml); sample name: 3A
fraction 30 to 75 (ca. 230 ml); sample name: 3B
fraction 76 to 97 (ca. 92 ml); sample name: 3C
fraction 98 to 130 (ca. 132 ml); sample name: 3D.

The precipitation found in pool 98 to 130 is stored at −20° C.

Total material through gel filtration is appr. 50%×50% of 90 mg=appr. 22.5 mg.

Samples A through D were presented for testing with the biological testing system using primary cells as described, each sample estimated at 5 mg (incl. losses).

Estimation of weight of substance of the samples, is as follows:

Sample 3A: 83 ml, containing 5 mg, concentration 60 $\mu$g/ml.
Sample 3B: 230 ml, containing 5 mg, concentration 22 $\mu$g/ml.
Sample 3C: 92 ml, containing 5 mg, concentration 54 $\mu$g/ml.
Sample 3D: 132 ml, containing 5 mg, concentration 38 $\mu$g/ml.

From Sample 3A a fraction of 0.625 ml was added to 2.9 ml destilled water, 1 ml of 5 times concentrated Iscove's Modified Dulbecco's medium (IMDM) and 0.5 ml Foetal Calf serum (FCS), thus resulting in a solution with a concentration of 1 $\mu$M.

From Sample 3B a fraction of 1.7 ml was added to 1.8 ml destilled water, 1 ml of 5 times concentrated IMDM and 0.5 ml FCS, thus resulting in a solution with a concentration of 1 $\mu$M.

From sample 3C a fraction of 0.694 ml was added to 2.8 ml destilled water, 1 ml of 5 times concentrated IMDM, and 0.5 ml FCS, thus resulting in a solution with a concentration of 1 $\mu$M.

From sample 3D a fraction of 0.987 ml was added to 2.5 ml destilled water, 1 ml of 5 times concentrated IMDM, and 0.5 ml of FCS, thus resulting in a solution with a concentration of 1 $\mu$M.

All fractions were filtered through a 0.22 $\mu$M filter before use.

The results are represented in tables and attached hereto. Sample 3A is represented in Tables 3 and 4 in FIG. 4, Sample 3B in Tables 5 and 6 in FIG. 5, Sample 3C in Tables 7 and 8 in FIG. 6, and Sample 3D in Tables 9 and 10 in FIG. 7.

Results of biologic testing on Samples 3A through 3D.

Only Sample 3D showed a dose dependent inhibition of replication of both virus isolates under study. Inhibition was complete (100%) at a concentration of 0.125 $\mu$M.

Sample 3D, originally consisting of 132 ml, of which almost 1 ml was used in the biologic test system, was further analysed by HPLC in a TFA system.

The TFA-HPLC system comprises a nucleosil 10C18 column having a length of 150 mm and a diameter of 2 mm in an HP 1090M apparatus, whereby the flow is at a 350 $\mu$l/min rate. The eluens is a gradient of 100% A/0% B to 100% B and 0A in 120 minutes whereby eluens A is 0.05% TFA (trifluoroacetic acid) in destilled water and eluens B is 0.03% TFA in acetonitrile.

Figure 9:
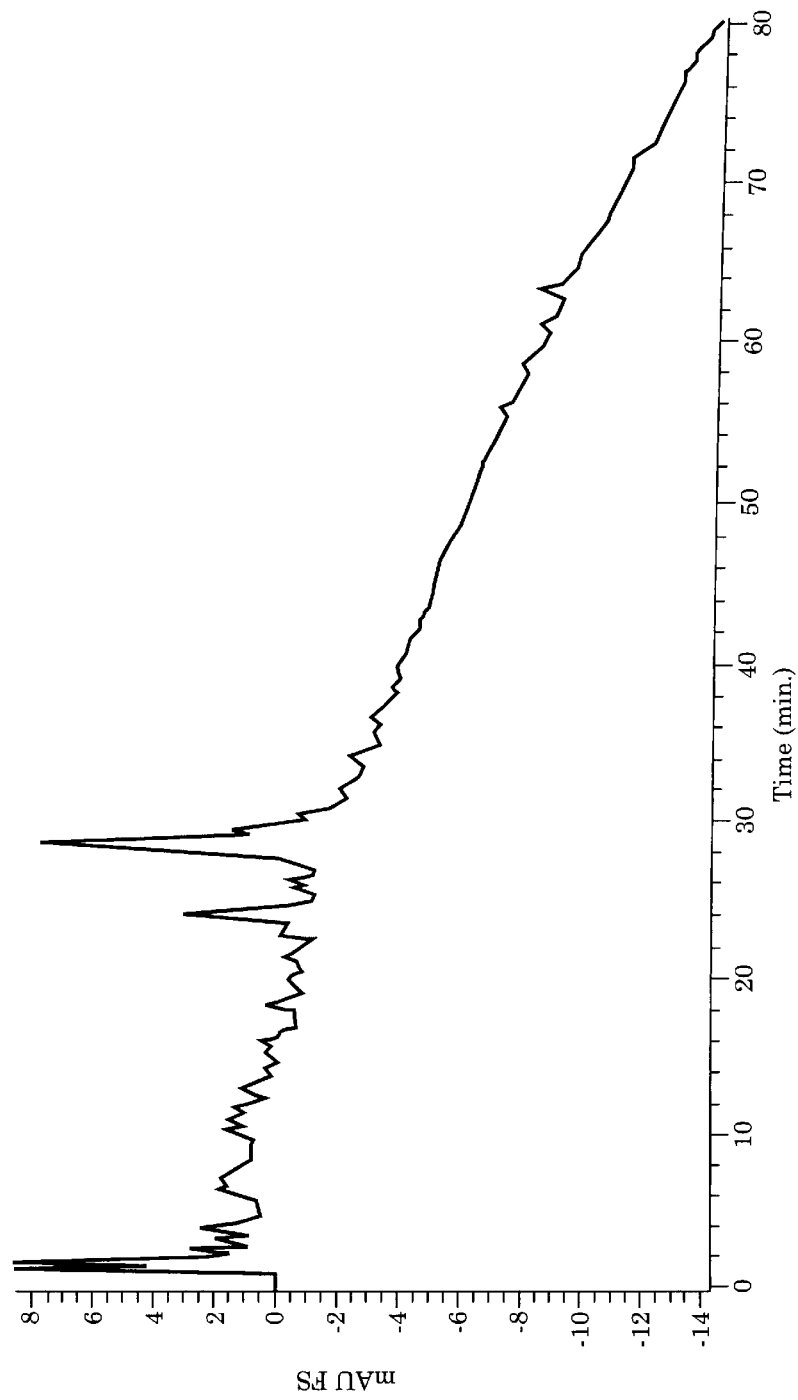
Figure 10:
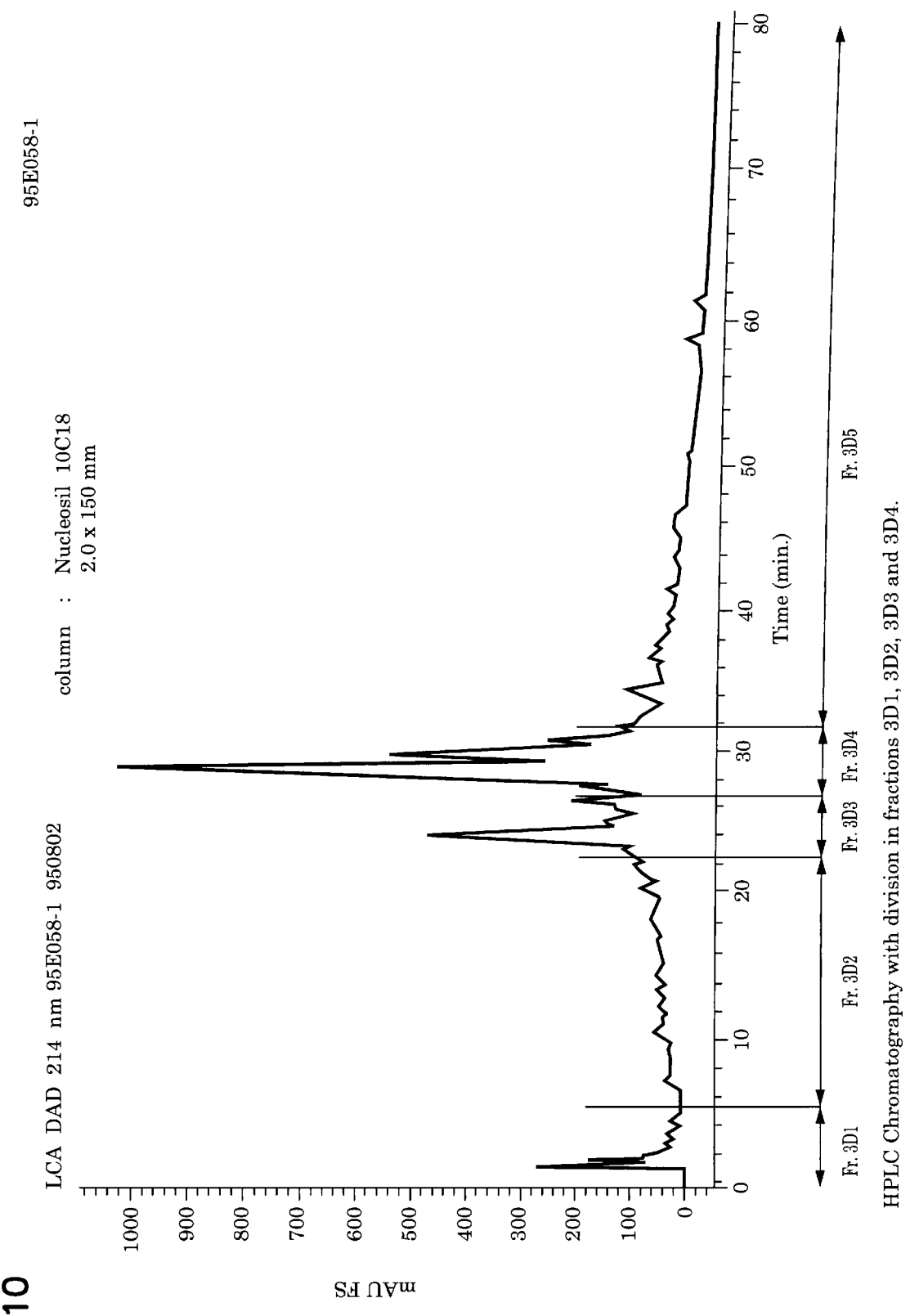

This sample, consisting of ca. 130 ml, was lyophilized, after retaining 1400 $\mu$l. The lyophilized substance was resuspended in 1 ml destilled water and centrifuged. 0.1% of the supernatant was examined on the analytical HPLC (result see graph 95E038 in FIG. 8), and 10% of the supernatant was separated following preparative HPLC (result see graph 95E043 in FIG. 9). Five fractions were isolated, lyophilized, resuspended in water, and lyophilized again. These fractions were named 3D1, 3D2, 3D3, and 3D4 (see FIG. 10), fraction 3D5 was stored at −20° C. Samples of fractions 3D3 and 3D4 was analysed by sequence analysis, no sequence was detectable in either fraction.

Fractions 3D1, 3D2, 3D3 and 3D4 were presented for testing at the biologic test system as described hereabove. Estimation of fraction quantities after HPLC, and based on the chromatogram, were: respectively: 120 $\mu$g, 30 $\mu$g, 30 $\mu$g, 50 $\mu$g and 50 $\mu$g.

Results of the test on HIV replication inhibition with these fractions are represented in Tables 11 to 18 (FIGS. 1–18).

It was concluded, that subfractions 3D3 and 3D4 showed an inhibitory effect on the replication of the two primary HIV isolates. Inhibition by subfraction 3D3 was complete at a concentration of 0.25 $\mu$M. Inhibition by subfraction 3D4 was complete at a concentration of 0.063 $\mu$M.

Fraction 3D3 and 3D4 were further analyzed by HPLC.

Figure 19:
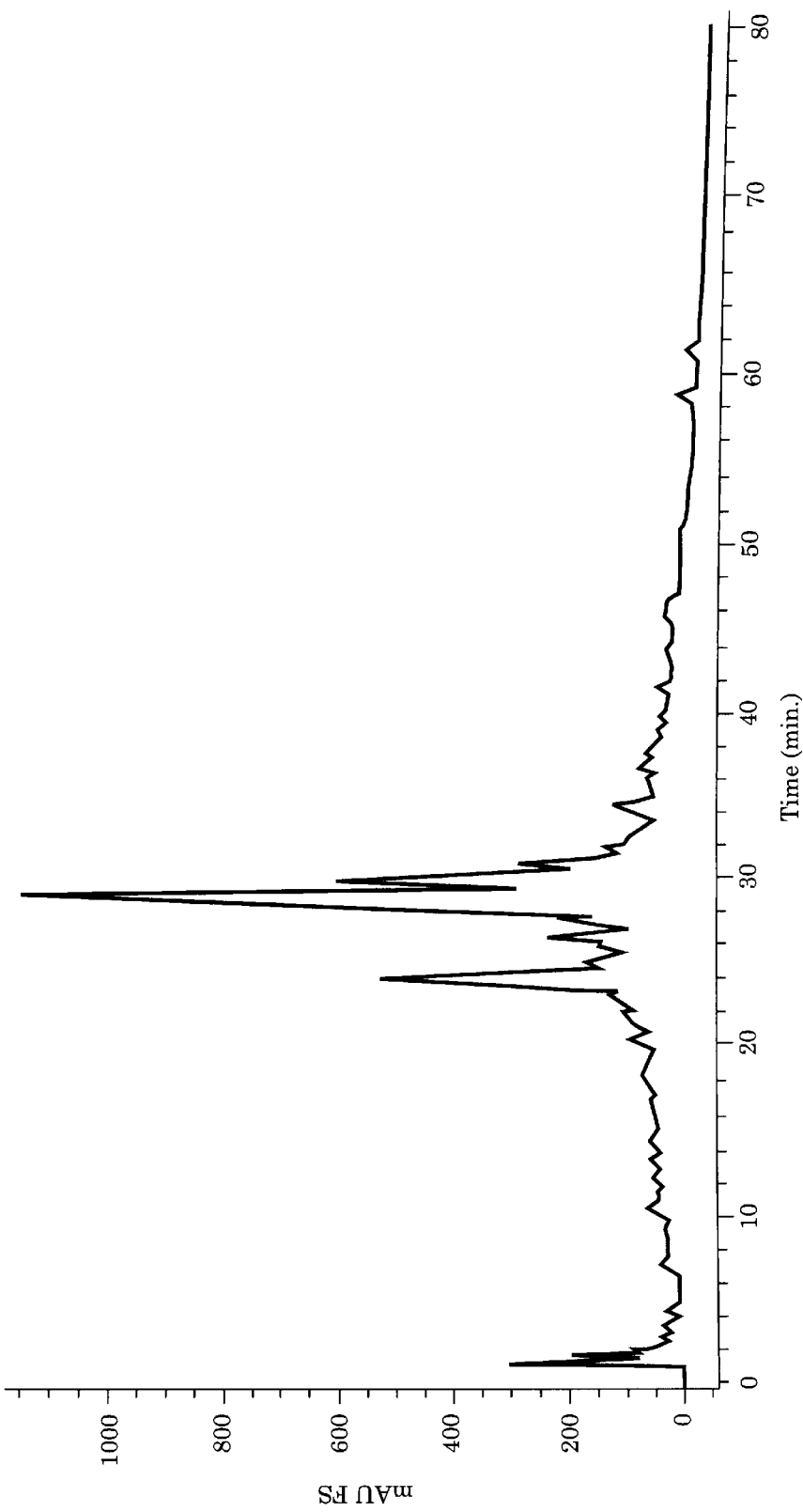
Figure 20:
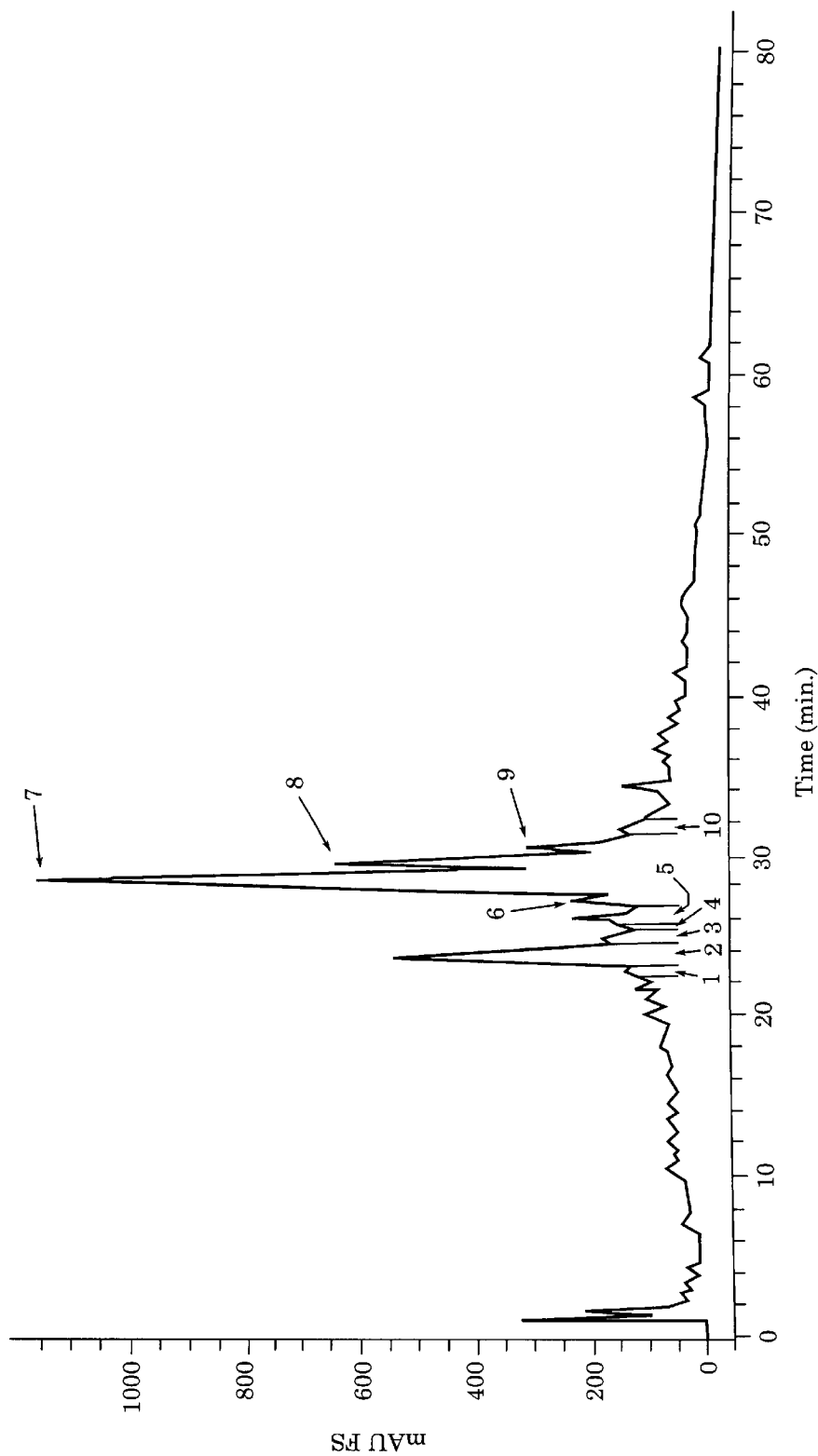

Therefore, from Sample 3D, (as specified hereabove), two time 10% was taken as starting material. Two preparative HPLC (same technique as before) runs were performed (see chromatogram 95E)58-2, FIG. 19). 10 fractions were separately isolated (no's 1 through 10 ) within 22 and 32 minutes elution time (see chromatogram with fractions in FIG. 20). Four out of these fractions, no's 6, 7, 8 and 9 were lyophilized, resuspended in destilled water and again lyophilized and were again presented for testing in the biologic system as described hereabove.

Estimation of fraction quantities gave: 1 $\mu$g, 39 $\mu$g, 7.5 $\mu$G and 2.5 $\mu$g respectively. Three fractions (6, 8 and 9) were solved in 1 ml medium (IMDM)+10% FCS, thus resulting in stock solution of 0.2 $\mu$M for fraction 6, 1.5 $\mu$M for fraction 8, and 0.5 $\mu$M for fraction 9. 50 (1 of these stock solution were added to 100 $\mu$l medium, providing final concentrations of 0.067 (M for fraction 6, of 0.5 $\mu$M for fraction 8, and of 0.17 $\mu$M for fraction 9. A dilution range was made only from fraction 7 (0.5 $\mu$M, 0.25 $\mu$M, 0.125 $\mu$M and 0.063 $\mu$M).

These four fractions were now renamed: $\alpha$, $\beta$, $\gamma$ and $\delta$ respectively.

Results were: complete (100%) HIV replication inhibition for fractions $\alpha$, $\beta$, $\gamma$ and $\delta$ at the concentration as tested. A dose dependent inhibition was observed for fraction $\beta$, being complete at a concentration of 0.5 $\mu$M (see Tables 19 to 22 in FIGS. 21–24).

In a further experiment, it was demonstrated, that from fraction $\beta$, a number of fractions could be isolated. Therefore, fraction 3D4$\beta$, as isolated from HPLC chromatography 95E058-2, was passed on a RP-HPLC in ammonium acetate.

The HPLC step comprises the same column as described for the TFA-HPLC at the same flow rate, the eluens is also a gradient running from 100% A and 0% B to 100% B and 0% A in 120 minutes, whereby A and B in this system are 0.1% ammonium acetate in destilled water at pH=6 (A) and 100% acetonitrile (B).

Figure 25:
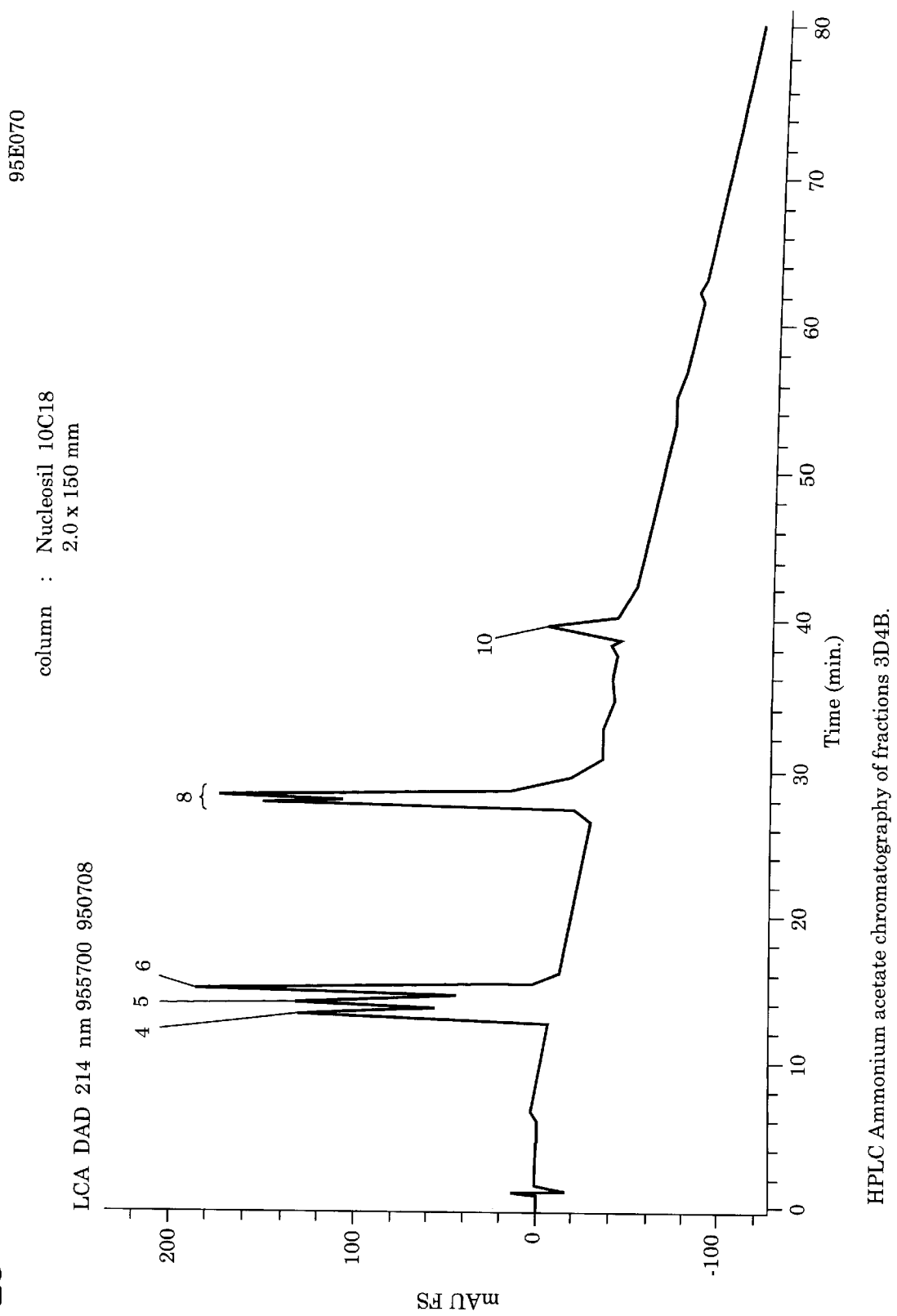

The result of this new chromatography is displayed in chromatogram: 95E070 (see FIG. 25).

Mass spectrometry of the fractions 3d3 and 3d4 (subfractions 1 through 10) showed molecules with masses of between 400 and 500 Dalton.

Subfractions 4, 5, 6, 8 and 10 were presented to be tested in the same biologic testing system as described above.

Test results showed low HIV replication inhibition activity for subfractions 4, 5, 6 and 10 up to a concentration of 0.06 $\mu$M. Subfractions 8 showed a dose-dependent inhibition of HIV replication with 100% inhibition for HIVams55 and 90% inhibition for HIVams37 at a concentration of 0.046 $\mu$M.

Subfraction 8 underwent a series of tests for mass spectrometry. It was determined, that this subfraction consisted of a mixture of two molecules with masses of 426 and 440 D.

ES/MEMS measurements for subfraction $8^{426}$ and $8^{440}$ showed positive productions of the following masses: both had a group of 120 D, a group of 17 D, a group of 18 D, and a group of 11 D. They differed in a group of 42 D for $8^{426}$, versus a group 56 D for $8^{440}$. No negative ions were detected.

Mass spectrometry of other fractions in Samples 3d3 and 3d4 (subfractions 1 through 10) showed molecules with masses of approximately 500 Dalton.

An Electrospray High Resolution Mass Spectrometry (ES-HRMS) was executed on the substances which showed HIV replication inhibition (subfraction 8, Siliavir). These were defined earlier herein by methods for isolation, purification and biological testing.

10% of subfraction 8 from HPLC 95E085 (solubilized in 0.1% TFA) was used therefore.

Figure 26:
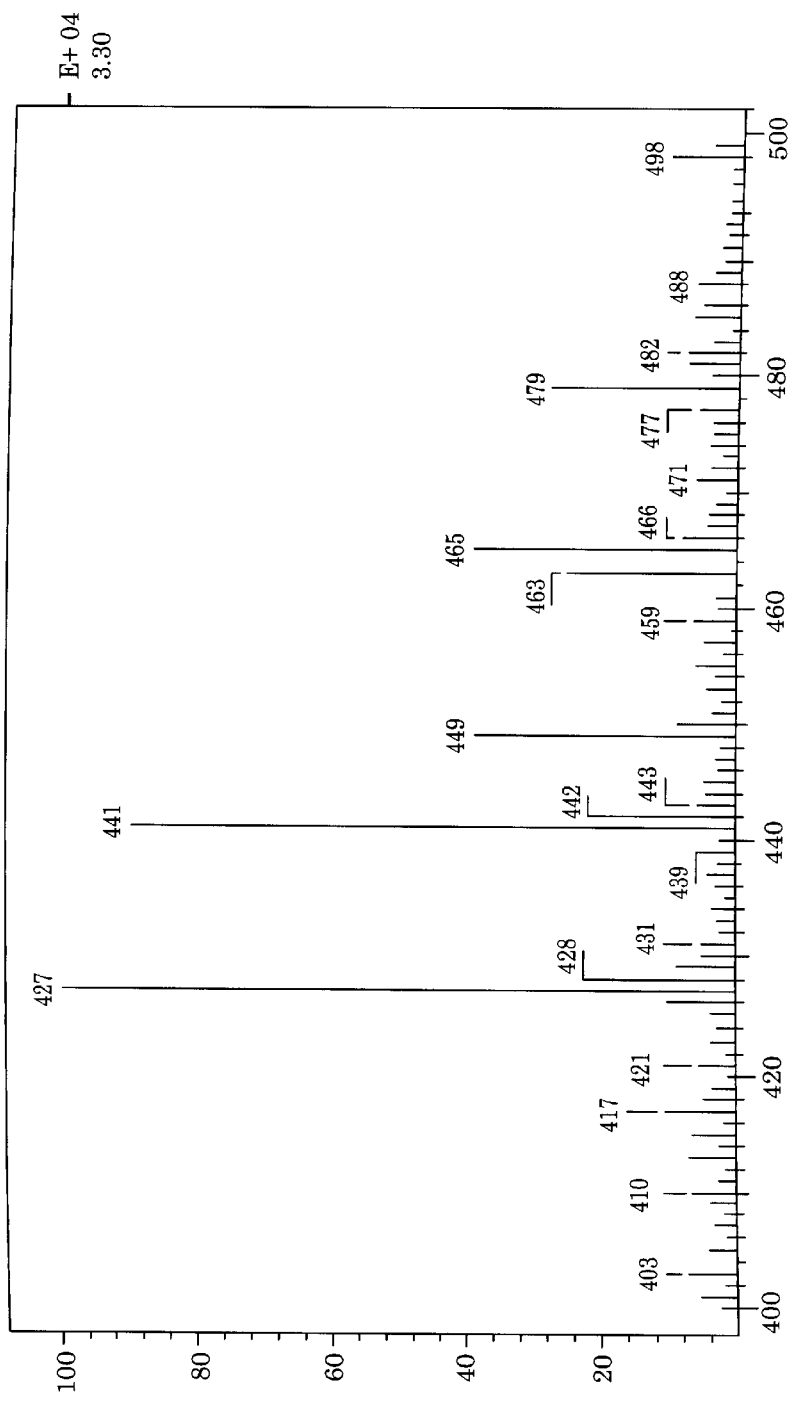

Two separate molecules were found as main fractions. One of these two molecules had the mass of 426.164300 D (subfraction $8^{426}$ or Siliavir$^{426}$), the other of the two molecules with the mass of 440.1816 D (subfraction $8^{440}$ or Siliavir$^{440}$). (See FIG. 26). The experiment was executed with a Finnigan-MAT 900 instrument at the resolution power of R=10,000. Consequently a sequential mass spectrometry (LC–MS)$^n$ was executed, and which confirmed earlier findings of ES-MSMS measurements.

Nuclear Magnetic Resonance (NMR)

NMR was executed on Siliavir with a Varian Unity 500 Mhz instrument. A sample was prepared from new base material for which raw leech head ethanol extracts were prepared as before. The lyophilized base material was resuspended with 50 ml $H_2O$. A separative step was performed to separate masses below and above 3kD. Therefore, this resuspended solution was repartitioned over 8 centriprep-3 (kD) tubes and centrifuged 4 times. Filtrates from each filtration step were combined, lyophilized and consequently resuspended in 50% HAC.

Figure 27:
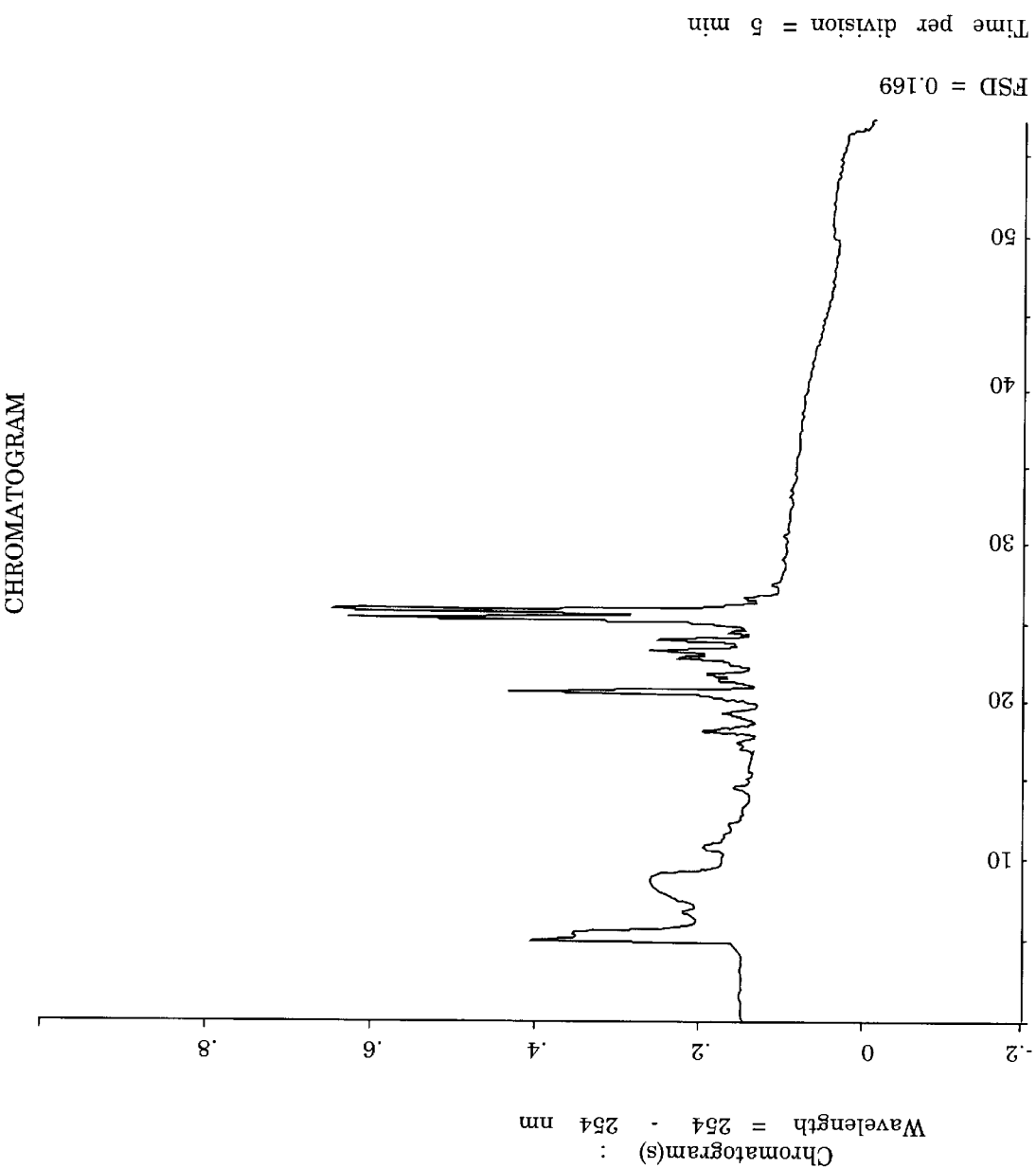

Subsequently, as was described herein before, preparative HPLC was performed on the resuspended filtrate. Column 7.7×250 mm (Nuceosil 10C18; flow adjusted at 2 ml/min; detection at 254 nm or 280 nm; TFA system; eluent A is 0.05% TFA; eluent B is 0.05% TFA in 100% acetonitrile; gradient: 0% B to 100% B in 60 minutes). The fraction at between 24.2 and 27 minutes was collected separately (see analytical HPLC FIG. 27) and lyophilized.

This fraction, as separated, was resuspended in 500 μl 50% Hac, and passed again at HPLC, with the ammonium acetate system. (Column 7.7×250 mm: nucleosil 10C18, flow adjusted at 2 ml/min, detection at 254 nm; Ammonium Acetate (A.A.)-system; eluent A is 0.1% A.A. in $H_2O$ at pH=6; eluent B is 100acetonitrile in 60 minutes).

Figure 28:
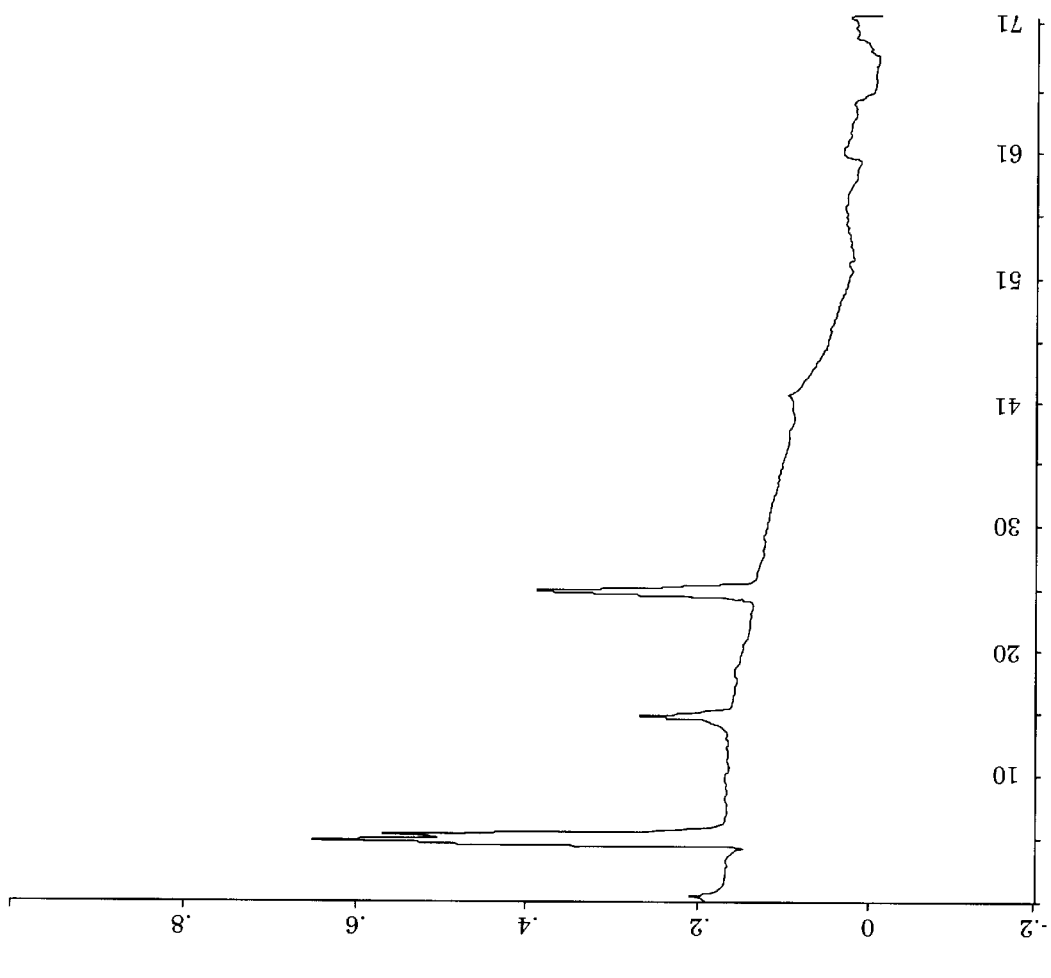
Figure 29:
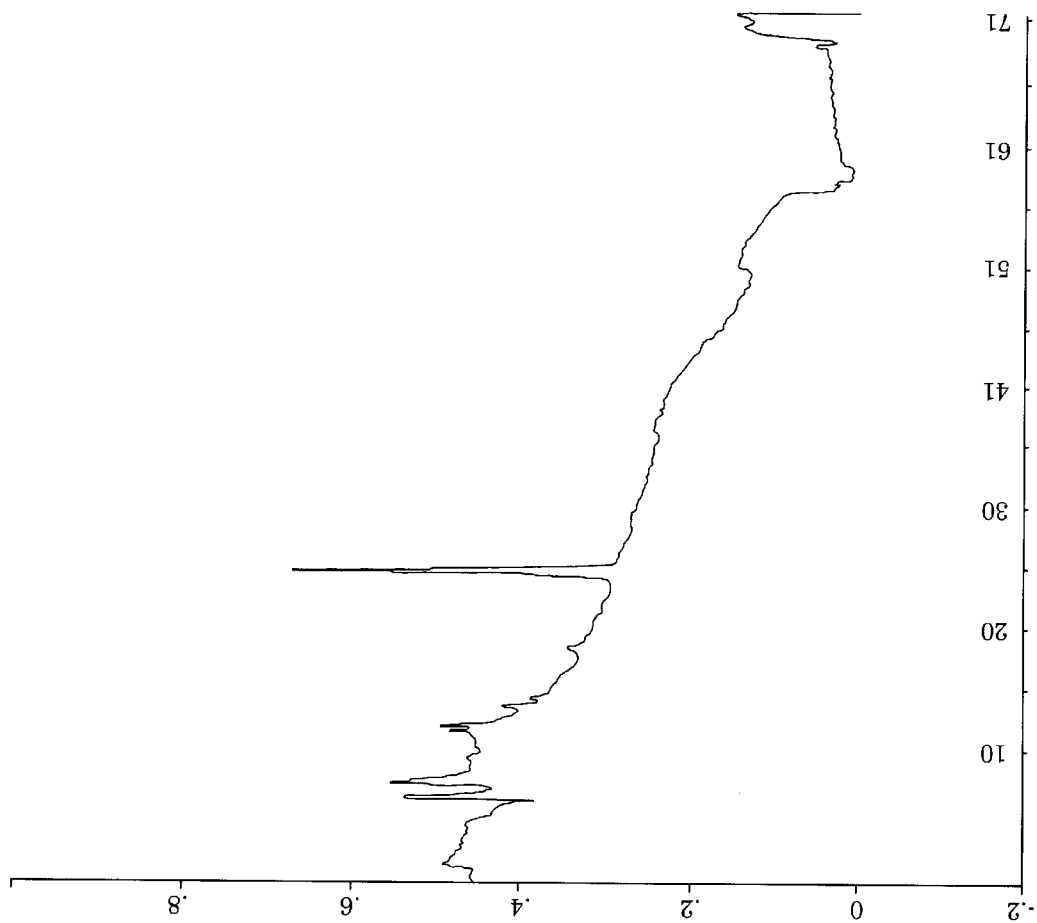

As this sample showed a time dependent precipitation, it was centrifuged and supernatant and pellet were analysed separately (See FIG. 28 for chromatogram of supernatant, and FIG. 29 for chromatogram of the pellet, which was resuspended in 1.6 ml 50% HAC).

Figure 30:
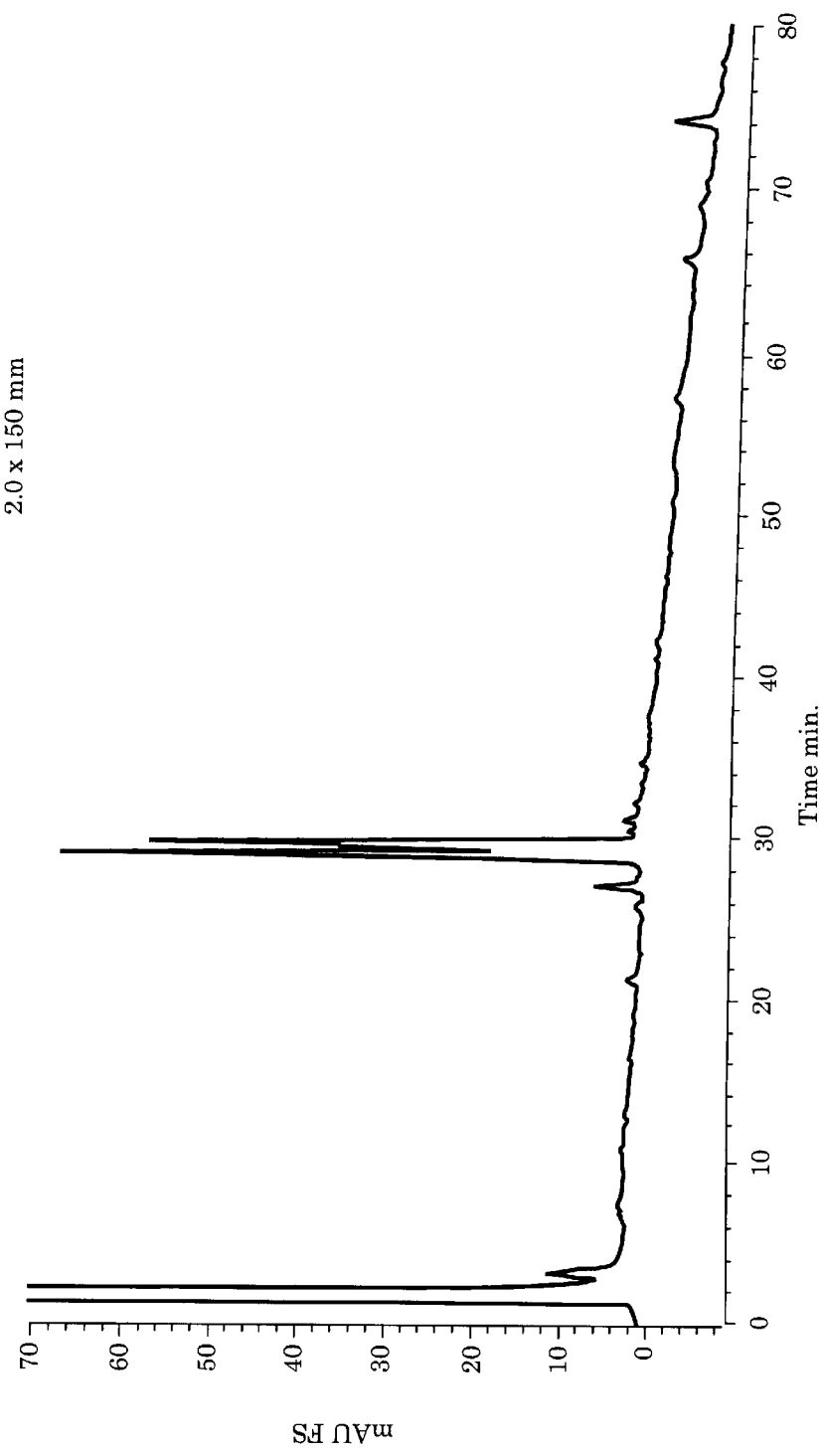
Figure 31:
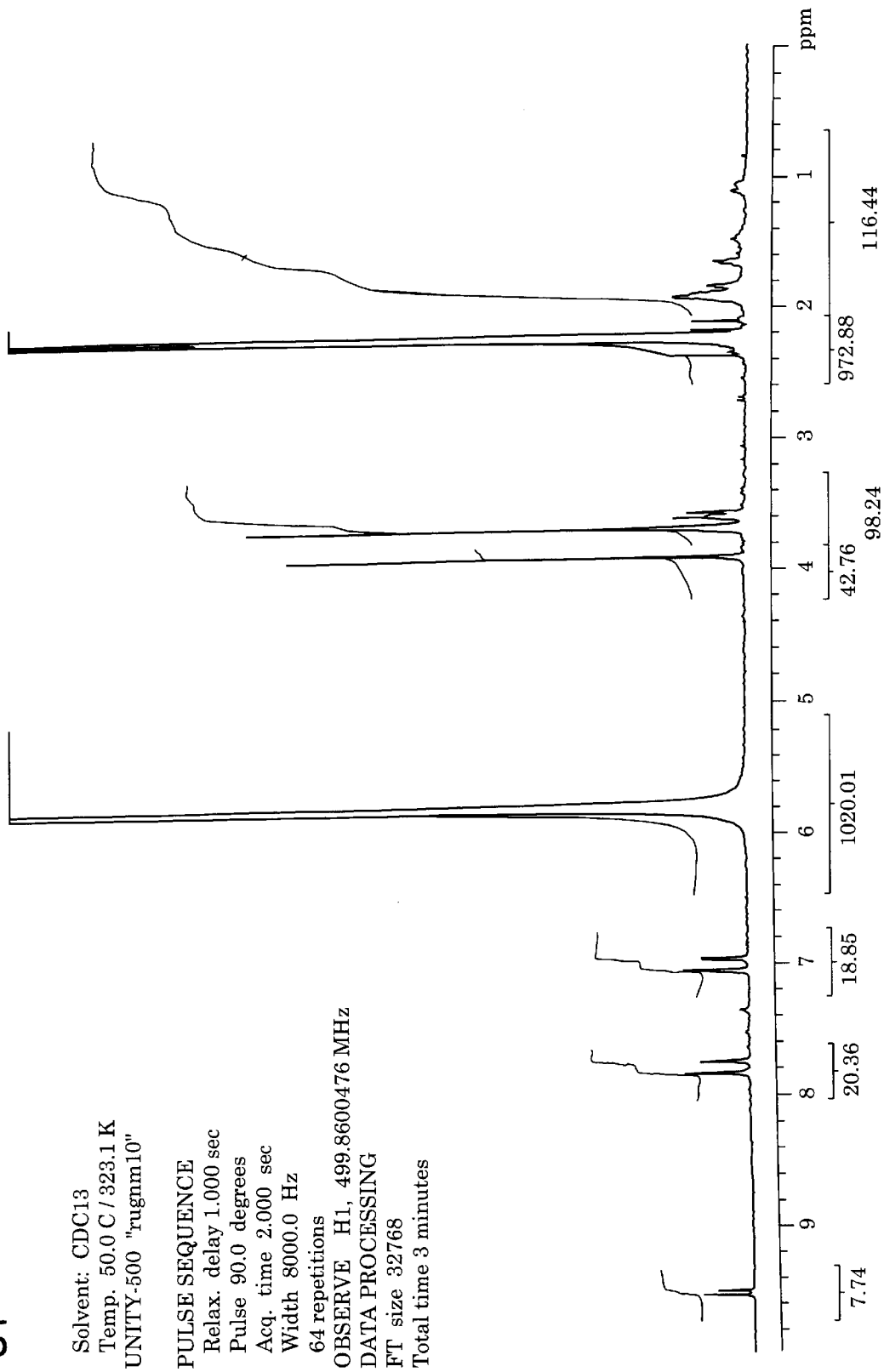
Figure 32:
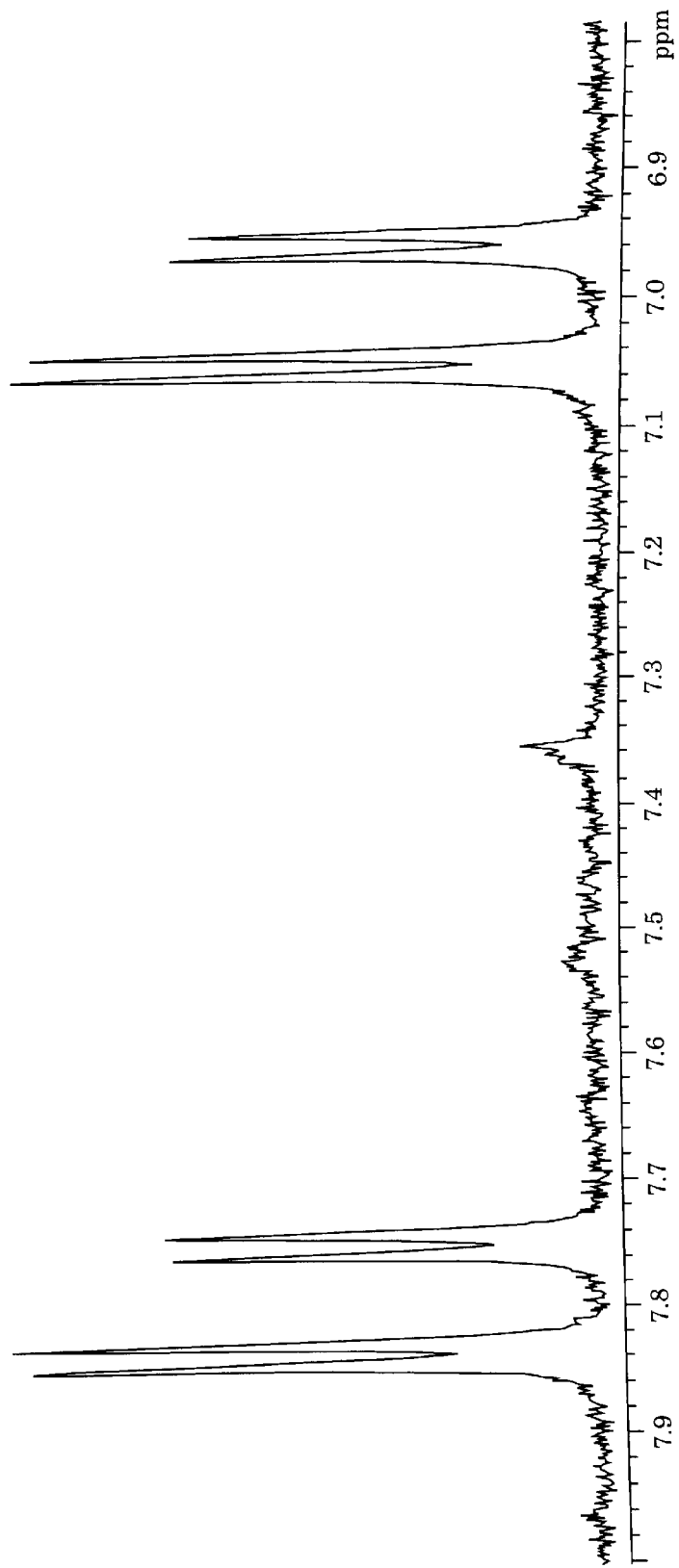
Figure 33:
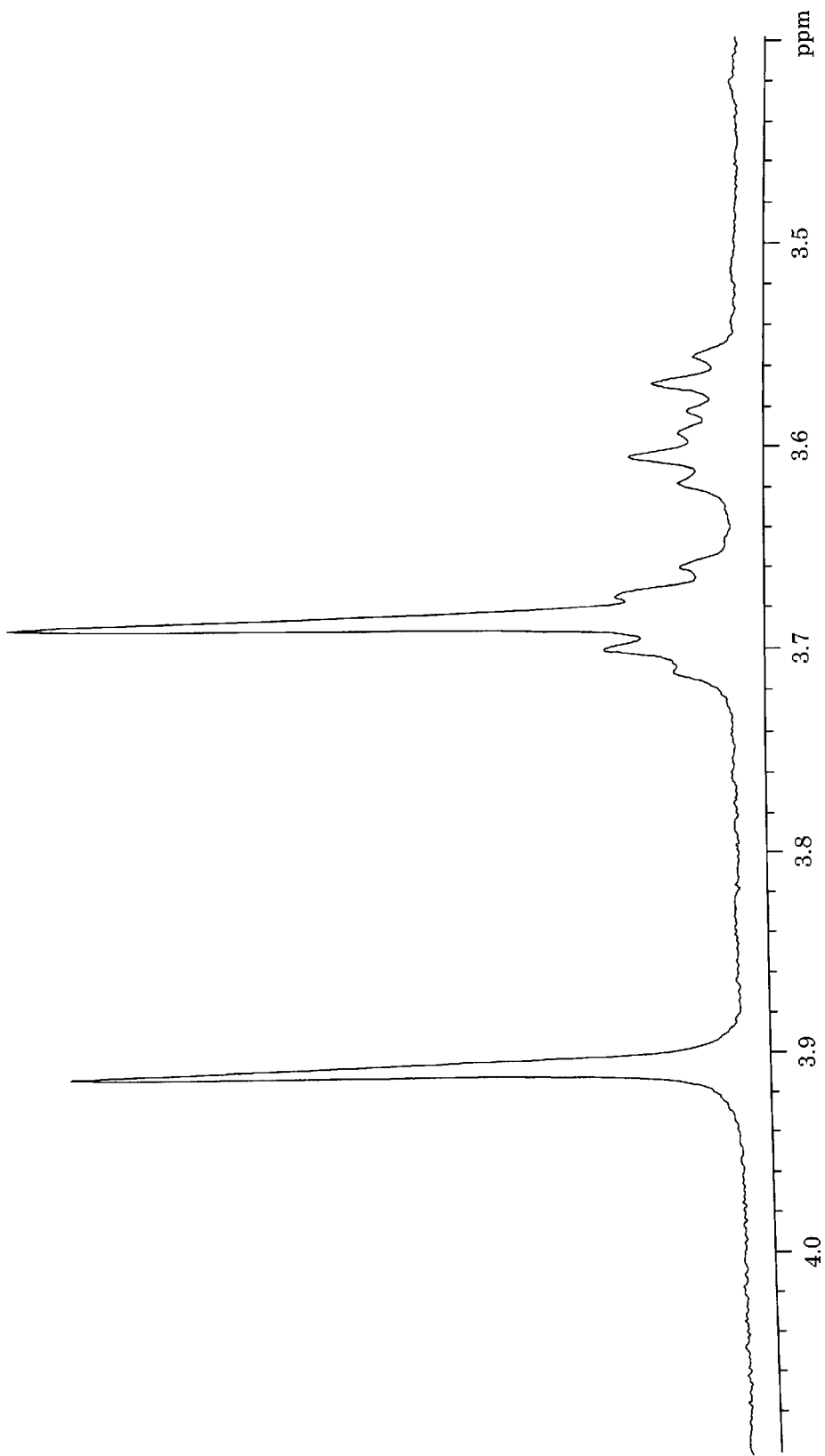
Figure 34:
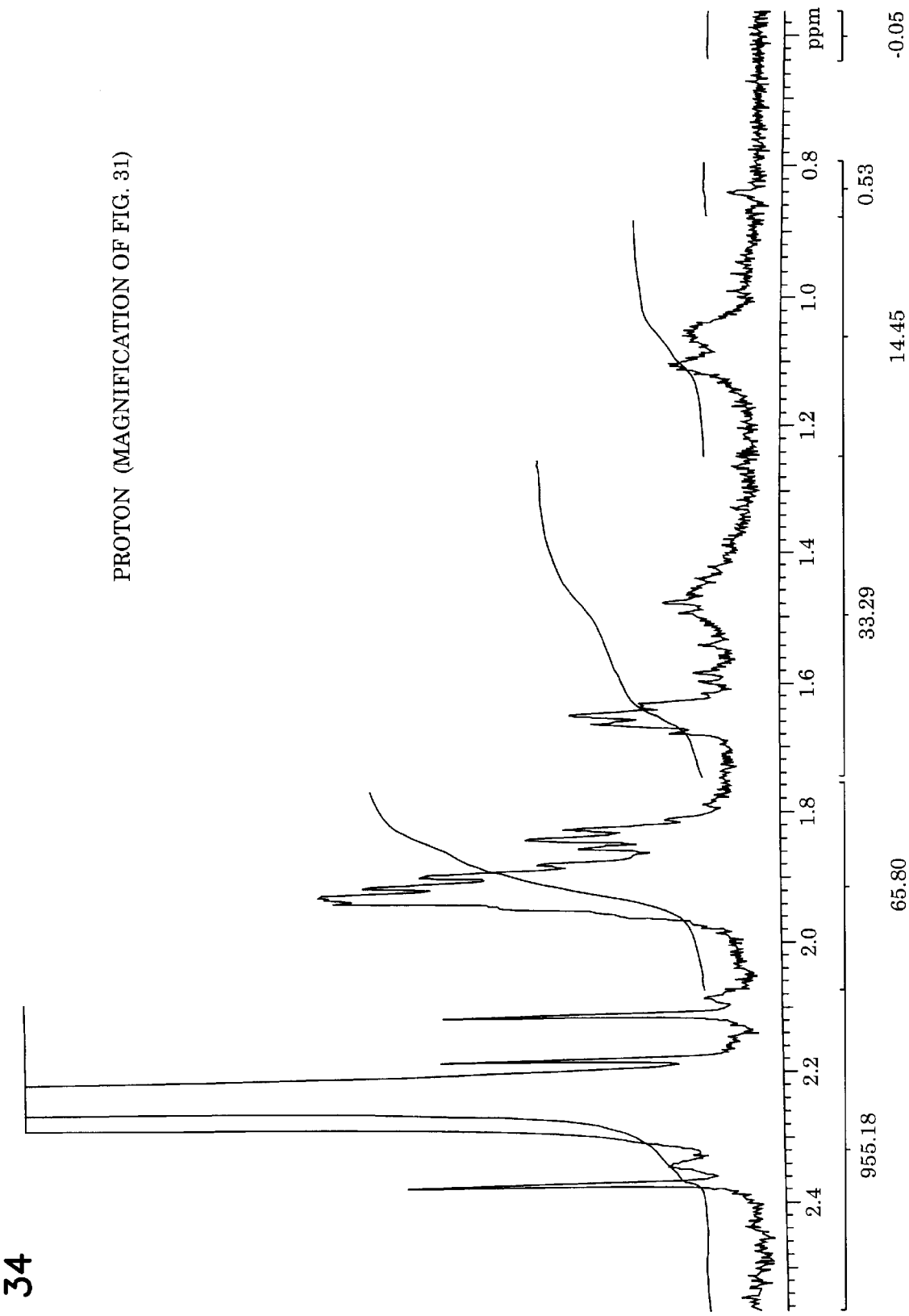

Fractions which eluted between 24 and 27 minutes from both the supernatant passage on HPLC and the pellet passage on HPLC were collected, combined and lyophilized. An analytical HPLC chromatogram of this collected material, consisting of both components Siliavir$^{426}$ and Siliavir$^{440}$, is shown in FIG. 30.

The material as described was prepared and resuspended with $D_2O$ and 50% DAc for passage on the Varian Utility 500 Mhz instrument. Separately, the resuspended pellet from FIG. 29 hereabove was also separately passed on the same instrument. Different types of NMR-Spectra (Proton, C13, DQCosy, HSQc, and Noesy) were made. The results are shown in FIGS. 31–41 for the spectra of both components together, while the results for the resuspended pellet (where one component, presumably Siliavir$^{426}$, is present for 85% in the sample, and the other component, presumably Siliavir$^{440}$, is present for only 15%) are shown in FIGS. 42–49.

Scanning Electron Microscopy/Energy Dispersing Spectroscopy (SEM/EDS)

The instrument used for this experiment was an (Akhashi) ISIDS-130. Preparation of the testmaterial was performed with both components (Siliavir$^{426}$ and Siliavir$^{440}$). The spectra showed peaks for C, N, and O. Moreover, a Si peak is shown, which probably derives from HPLC column material although it cannot be excluded that it derives from the active compound. The presence of S in the spectrum can be attributed to a derivative of the compound, e.g. a salt, but may also be a pollution. No P was found.

Results of NMR, MS and EMS/EDS and discussion

Discussed are the results in the NMR measurements on the test material consisting of the mixture of the two components (as shown in FIGS. 31–41) and of the NMR measurements on the material consisting of 85% of one component and 15% of the other component (as shown in FIGS. 42–49).

Singlet at 9.3 ppm correlates in HSQC at 148 ppm. This may be an isolated aromatic CH between 2 N's.

Two doublets at 6.75 and 7.54 ppm: 2±2 protons couple with 8.5 Hz. This constant is comparable to tyrosine, and therefore points towards a para substituted aromatic ring.

This phenylfragment has two substituents, probably no direct C's as interaction in Noesy spectrum is missing.

Two singlets at 3.5 and 3.7 ppm; 2±3 protonen. No DQCosy and/or Noesy interactions. Correlations in HSQC at ca. 30 ppm. These are probaby N—$Ch_3$ groups, and probably not O—$CH_3$ groups. Because of their position in the low field, a dimethylated hetero aromatic Z-ring system, e.g. a xanthine-like fragment (a purine alkaloid), is a probable explanation for these peaks in conjunction with the 9.3 ppm peak.

One triplet at 3.7 ppm: 2 protons. Correlates in DQCosy with a multiplet at 1.72 ppm (2 protons); this multiplet correlates with the multiplet at 1.46 ppm (2 protons).

One triplet at 3.4 ppm: 2 protons. Correlates in DQCosy with a multiplet at 1.65 ppm (2 protons); this multiplet correlates with the same multiplet at 1.46 ppm (2 protons).

It is concluded from these triplets and multiplets that this may point towards a Xl—$(Ch_2)_{5-x}$5 fragment, in which $X_1$ and $X_2$ are most probably N, based on the chemical shift positions of the alpha $Ch_2$'s.

Signals at 1.2 and 1.4 ppm: probably artefacts or pollution.

Sulphur atoms are not likely to be present from these NMR spectra.

The NMR signals of the two components show that these are isomers. They only differ 14.0173 D, which can only represent $CH_2$. Therefore, it is concluded that Siliavir$^{440}$ is equal to Siliavir$^{426}$ plus $CH_2$.

The presence of the following groups is concluded or presumed:

A para-substituted aromatic ring, mass=76+$Y_1$+$Y_2$.

AB system in aromatic ring, e.g. of the formula:

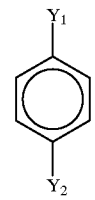

wherein $Y_1$ can for instance be —OH, —$CH_2OH$, —=C=O or —C(O)H, while $Y_2$ can be an oxygen atom, a NH-group, an N-group substituted by $C_{1-3}$ alkyl or $C_{1-3}$ (substituted) alkyl, C=).

A pentane fragment in the 426 component, possibly hexane in the 440 component, e.g. of the formula:

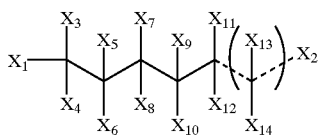

wherein $X_1$ and $X_2$ may e.g. be: C, N, $NCH_3$, $NSO_4$, and $X_3$ to $X_4$ may e.g. be: H, $NH_2$, N=C=O or $X_3+X_4$, $X_5+X_4$, $X_5+X_6$, $X_7+X_8$, $X_9+X_{10}$, $X_{11}X_{12}$, $X_{13}+X_{14}$ may together be an oxygen or a =NH-group.

A methylated aromatic heterocyclic, e.g. xanthine-like fragment, with two $CH_3$ groups, e.g. of the type:

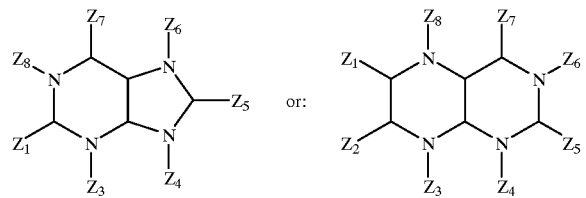

wherein $Z_1$, $Z_2$, $Z_5$, $Z_7$ may e.g. be: C, H, $CH_2OH$, $NCO_3$; and $Z_3$, $Z_4$, $Z_6$, $Z_8$ may e.g. be: C, H, $CH_3$, OH, $CH_2OH$.

A C—H between two N'S.

Based on the above presumptions the acive compounds may be compounds of the types:

wherein "O" is a carbon atom substituted with one or two hydrogen atoms.

Conclusion

It can be concluded, that HIV replication inhibition is strongly present in a group of substances, which can be attributed in separate isolates or molecules, or combination of molecules within this group. The group of substances is described herein-above by methods for isolation and biological testing.

The group of substances containing the HIV replication inhibition comprises e.g.:

3D3 and 3D4 as described. The molecules contained in this group of substances for the major part have molecular weights of around 500 Dalton.

Literature

Autrum H.: Bronn's Klassen und ordnungen des Tierreichs 1936 Berman P W. et al. : Nature 1990, 345: 622–625.

Blaise M.: J Med Vet Militaire 1874/5, 10.

Bucnocore L. & Rose J K: Nature 1990, 345: 625–628.

Harant H.: Arch Soc Sci Montpellier 1927, 10: 1–76 Jacks T. et al.: Nature 1988, 330: 280–283.

Jarry D.: Bull Soc Zool Fr 1959, 84: 73–76.

Keegan H. L. et al. : Am J Trop Med Hyg 1970, 19-6: 1029–1030.

Kohl N E. et al: Proc Natl Acad Sci USA 1988, 85: 4686–4690.

Loeb D D. et al.: Nature 1989, 340: 397–400.

Mouquin-Tandon A. : Monographie de la famille des Hirunidees, Paris, 1846.

Neveu-Lemaire.: Trate d'entomologie medicanale et veterinaire, 1938

Pauwels R. et al.: Nature 1990, 343: 470–474.

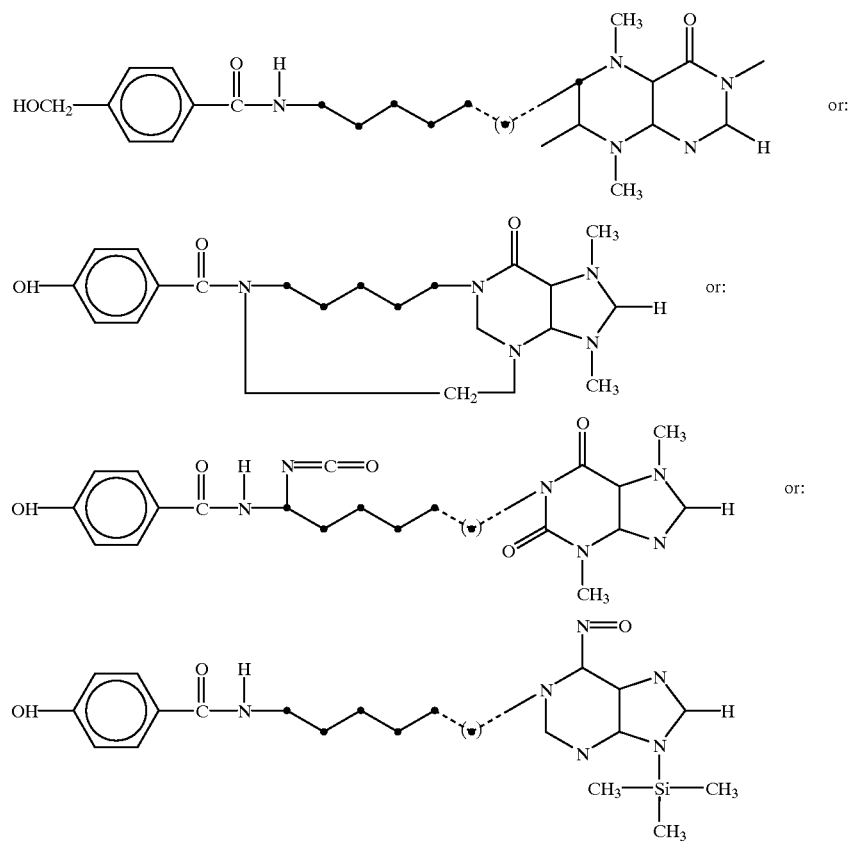

Rusche J R. et al.: Proc Natl Acad Sci USA 1985, 85: 3198–3202.
Shaw G M. et al.: Science 1984, 226: 1165—1171.
Turner F M. : the Lancet 1969, 1400–1401.
Veronese F D. et al.: J Virol 1988, 62: 795–801.

What is claimed is:

1. A method for obtaining an extract having inhibiting activity toward a human immunodeficiency virus, comprising:
   preparing a suspension from tissue of a leech from the family hirudinidae;
   fractionating the suspension; and
   selecting as the extract a protein-free fraction which exhibits a molecular weight in the range of 300 to about 600 Daltons and exhibits inhibiting activity towards a human immunodeficiency virus.

2. The method of claim 1, wherein preparing the suspension from tissue of a leech from the family hirudinidae comprises extraction with a solvent comprising ethanol.

3. The method of claim 2, wherein the solvent comprises ethanol and water.

4. The method of claim 1, further comprising:
   subjecting the fraction to further purification.

5. The method of claim 4, wherein further purification comprises:
   subfractionating said fraction to separate discrete subfractions; and
   selecting as the extract a subfraction exhibiting inhibiting activity towards a human immunodeficiency virus.

6. The method of claim 4, wherein further purification comprises separation on a HPLC column.

7. The method of claim 4, wherein further purification comprises separation on a HPLC column comprised of nucleosil 10C18.

8. The method of claim 1, further comprising:
   extracting leech tissue or secretions;
   lyophilizing the resulting solution;
   suspending the lyophilized material in an aqueous solution;
   centrifuging the suspension to obtain a pellet and a supernatant;
   loading resulting supernatant on a size fractionation column;
   eluting the column with an aqueous solution;
   saving fractions of the eluted material;
   testing the fractions for anti-viral activity; and
   collecting as the extract the active fractions.

9. The method of claim 8 wherein the size-fractionation column comprises Sephadex g-75.

10. The method of claim 1, further comprising:
    separating the fraction that exhibits inhibiting activity towards a human immunodeficiency virus on a first reverse phase HPLC column wherein the eluent is a gradient from a solution comprising trifluoracetic acid in water to a solution comprising trifluoracetic acid in acetonitrile;
    collecting a portion of the eluent corresponding to the major absorption peak of the chromatogram recorded at 254 nm;
    subjecting the portion to chromatography on a second reverse phase HPLC column wherein the eluent is a gradient from a solution comprising ammonium acetate in water to a solution comprising acetonitrile; and
    recovering an extract that exhibits inhibitory activity towards human immunodeficiency virus by collecting the eluent from the second reverse phase HPLC column corresponding to the major absorption peak or peaks of the chromatogram recorded at 254 nm.

11. A method according to claim 1, wherein the extract has inhibitory activity in the micromolar range.

12. A method according to claim 11, wherein the extract completely inhibits the human immunodeficiency virus induced syncytium formation or p24 production at 0.5 micromolar concentrations or less.

13. A method according to claim 12, wherein the extract has inhibitory activity of 0.17 micromolar concentrations or less.

14. A method according to claim 13, wherein the extract has inhibitory activity at 0.067 micromolar concentration.

15. An extract obtained by a method according to claim 1, wherein the extract exhibits a molecular weight between about 300 and about 600 Daltons.

16. The extract of claim 15, wherein the molecular weight is between about 400 and about 500 Daltons.

17. The extract of claim 15, wherein the extract has inhibitory activity in the micromolar range.

18. The extract of claim 17, wherein the extract completely inhibits the human immunodeficiency virus induced syncytium formation of p24 production at 0.5 micromolar concentrations or less.

19. The extract of claim 18, wherein the extract has inhibitory activity at 0.17 micromolar concentrations or less.

20. The extract of claim 19, wherein the extract has inhibitory activity at 0.067 micromolar concentration.

21. A pharmaceutical composition comprising an extract obtained according to claim 1, and a suitable vehicle for administration.

22. A method of inhibiting activity of a human immunodeficiency virus comprising contacting said virus with an extract obtained according to claim 1.

23. A method for obtaining an extract having inhibiting activity towards a human immunodeficiency virus, comprising:
    preparing a suspension from tissue of a leech from the family hirudinidae;
    fractionating the suspension; and
    selecting as the extract a protein-free fraction which exhibits a molecular weight in the range of 300 to about 600 Dalton and exhibits inhibiting activity towards a human immunodeficiency virus; and wherein said fraction is selected from the group of -continued

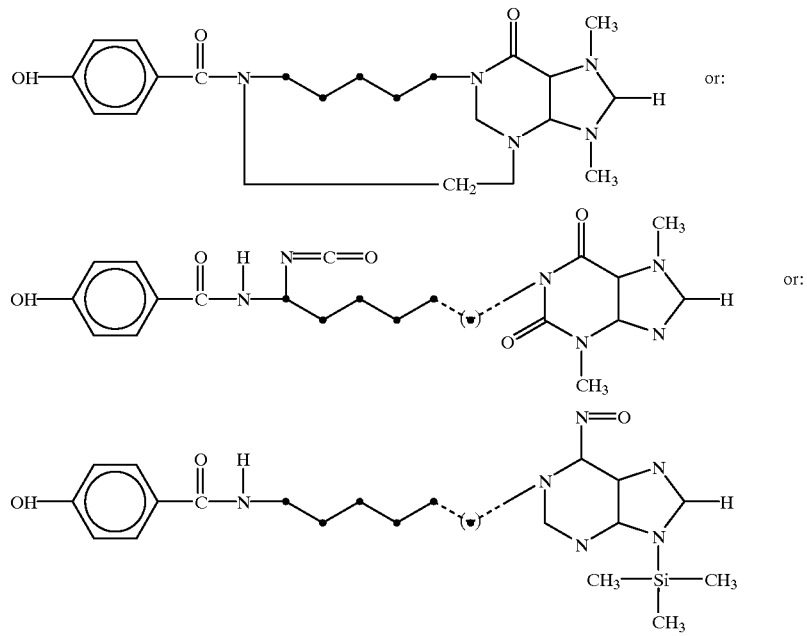

24. A method of obtaining an extract having inhibiting activity toward a human immunodeficiency virus, comprising:
preparing a suspension from tissue of a leech from the family hirudinidae;
fractionating the suspension; and
selecting as the extract a protein-free fraction which exhibits a molecular weight in the range of 300 to about 600 Daltons and exhibits inhibiting activity towards a human immunodeficiency virus; and wherein said extract is of the formula $Ar^1$-spacer-$Ar^2$, wherein $Ar^1$ is a six ring aromatic which is substituted with one or more of a hydroxyl group, an amino group, a $C_{1-4}$ alkyl group, or a halogen wherein—spacer—is a $C_{3-8}$ alkyl alkylene group coupled through a hydrophilic group to said $Ar_1$ group, and further wherein $Ar^2$ is a heteroaromatic 2-ringsystem of carbon and nitrogen atoms, said 2-ringsystem having form 9 to 10 atoms in a purine-like or naphthalene-like ringsystem, and said 2-ringsystem is substituted with one or more of a $C_{3-8}$ alkyl group, a hydroxy group, an amino group, or a halogen group.

* * * * *